US012685596B2

(12) United States Patent
Ziv-Ari et al.

(10) Patent No.: US 12,685,596 B2
(45) Date of Patent: Jul. 21, 2026

(54) SYSTEM AND METHOD TO DETERMINE THE LOCATION OF A CATHETER

(71) Applicant: BIOSENSE WEBSTER (ISRAEL) LTD., Yokneam (IL)

(72) Inventors: Morris Ziv-Ari, Atlit (IL); Assaf Cohen, Bialik (IL); Itai Doron, Katsir (IL); Meir Bar-Tal, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 746 days.

(21) Appl. No.: 17/857,339

(22) Filed: Jul. 5, 2022

(65) Prior Publication Data

US 2022/0338939 A1 Oct. 27, 2022

Related U.S. Application Data

(63) Continuation-in-part of application No. 17/366,364, filed on Jul. 2, 2021, now Pat. No. 12,144,636.

(Continued)

(51) Int. Cl.
*A61B 34/20* (2016.01)
*A61B 5/367* (2021.01)
(Continued)

(52) U.S. Cl.
CPC .............. *A61B 34/20* (2016.02); *A61B 5/367* (2021.01); *A61B 18/1492* (2013.01); *G06N 3/08* (2013.01);
(Continued)

(58) Field of Classification Search
CPC ..................................................... A61B 34/20
(Continued)

(56) References Cited

U.S. PATENT DOCUMENTS 8,456,182 B2 6/2013 Bar-Tal et al.
12,131,424 B2 10/2024 Krummen et al.
(Continued)

FOREIGN PATENT DOCUMENTS

CN 108042129 A 5/2018
EP 2168478 A1 3/2010
(Continued)

OTHER PUBLICATIONS

International Search Report and Written Opinion mailed on Oct. 24, 2023 for PCT Patent Application No. PCT/IB2023/056924.
(Continued)

*Primary Examiner* — Nicole F Johnson
(74) *Attorney, Agent, or Firm* — Clayton, McKay & Bailey, PC

(57) ABSTRACT

Systems, devices, and techniques are disclosed for automatically generating CPM matrices. The system includes a processor configured to receive a plurality of historical, sparse CPM matrices and a plurality of historical, supplemented CPM matrices, wherein each sparse CPM matrix is associated with a respective supplemented CPM matrix; train a learning system based on the plurality of historical, sparse CPM matrices and the plurality of historical, supplemented CPM matrices, wherein the learning system is trained so as to generate a supplemented CPM matrix given a sparse CPM matrix; receive, by the trained learning system, a new, sparse CPM matrix; and generate, with the trained learning system, a new supplemented CPM matrix.

18 Claims, 26 Drawing Sheets

Related U.S. Application Data

(60) Provisional application No. 63/049,191, filed on Jul. 8, 2020.

(51) Int. Cl.

| | | |
|---|---|---|
| *A61B 18/14* | (2006.01) | |
| *G06N 3/08* | (2023.01) | |
| *A61B 18/00* | (2006.01) | |
| *A61M 25/01* | (2006.01) | |

(52) U.S. Cl.
CPC .............. *A61B 2018/00577* (2013.01); *A61B 2034/2053* (2016.02); *A61M 2025/0166* (2013.01)

(58) Field of Classification Search
USPC ......................................................... 600/508
See application file for complete search history.

(56) References Cited

U.S. PATENT DOCUMENTS

| | | | | |
|---|---|---|---|---|
| 2005/0182319 | A1 | 8/2005 | Glossop | |
| 2009/0088633 | A1 | 4/2009 | Meyer et al. | |
| 2014/0221803 | A1* | 8/2014 | Bar-Tal | A61B 5/063 600/373 |
| 2018/0296108 | A1* | 10/2018 | Stewart | G06F 40/169 |
| 2019/0090774 | A1 | 3/2019 | Yang et al. | |
| 2020/0179057 | A1* | 6/2020 | Turgeman | A61B 34/20 |
| 2020/0196908 | A1 | 6/2020 | Ben-Haim et al. | |
| 2022/0007989 | A1 | 1/2022 | Ziv-Ari et al. | |

FOREIGN PATENT DOCUMENTS

| | | | | |
|---|---|---|---|---|
| EP | 3937182 | A1 | 1/2022 | |
| EP | 4113528 | A1 | 1/2023 | |
| JP | 2022031248 | A | 2/2022 | |
| WO | WO-2019217430 | A1 * | 11/2019 | ....... A61B 17/22004 |
| WO | 2020181006 | A1 | 9/2020 | |

OTHER PUBLICATIONS

Extended European Search Report dated Dec. 1, 2021 for European Patent Application No. 21184148.1.

Thrissi et al.,"Data Augmentation for Automatic Identification of Spatiotemporal Dispersion Electrograms in Persistent 2 ¼atrial Fibrillation Ablation Using Machine Learning," 2020 42nd Annual International Conference of the IEEE Engineering in Medicine & Biology Society (EMBC), 2020, pp. 406-409 (Jul. 2020).

Lozoya et al., "Model-Based Feature Augmentation for Cardiac Ablation Target Learning From Images." IEEE ransactions on bio-medical engineering vol. 66,1: 30-40 (2019).

Lee et al., "A Deep-Learning System for Fully-Automated Peripherally Inserted Central Catheter (P1CC) Tip Detection." Pournal of digital imaging vol. 31,4: 393-402 (2018).

Walker et al.,"Utilization of neural networks for catheter tip position determination in intraventricular impedance 5 maging," Proceedings of 18th Annual International Conference of the IEEE Engineering in Medicine and Biology ociety, 1996, pp. 796-797 vol. 2(1996).

Cross-validation (statistics), https://en.wikipedia.org/wiki/Cross-validation_(statistics), Available at: https://web. irchive.orglweb/20200703082047/https://en.wikipedia.org/wiki/Cross-validation_(statistics) (Jul. 3, 2020).

2 Transfer learning, https://en.wikipedia.org/wiki/Transfer_learning, Available at: https://web.archive.org/ veb/2020070301 1 131/https://en.wikipedia.org/wiki/Transfer_learning (Jul. 3, 2020).

Universal approximation theorem, https://en.wikipedia.org/wiki/IJniversal_approximation_theorem, Available at: 3 ittps://web.archive.orglweb/20200525082913/https://en.wikipedia.org/wiki/lJniversal_approximation_theorem (May 25, !020).

* cited by examiner

300

500

Collect Data From Hardware —510

Train a Machine on the Hardware —520

Build a Model —530

Predict Outcomes of the Hardware —540

1630

1636

1632

1634

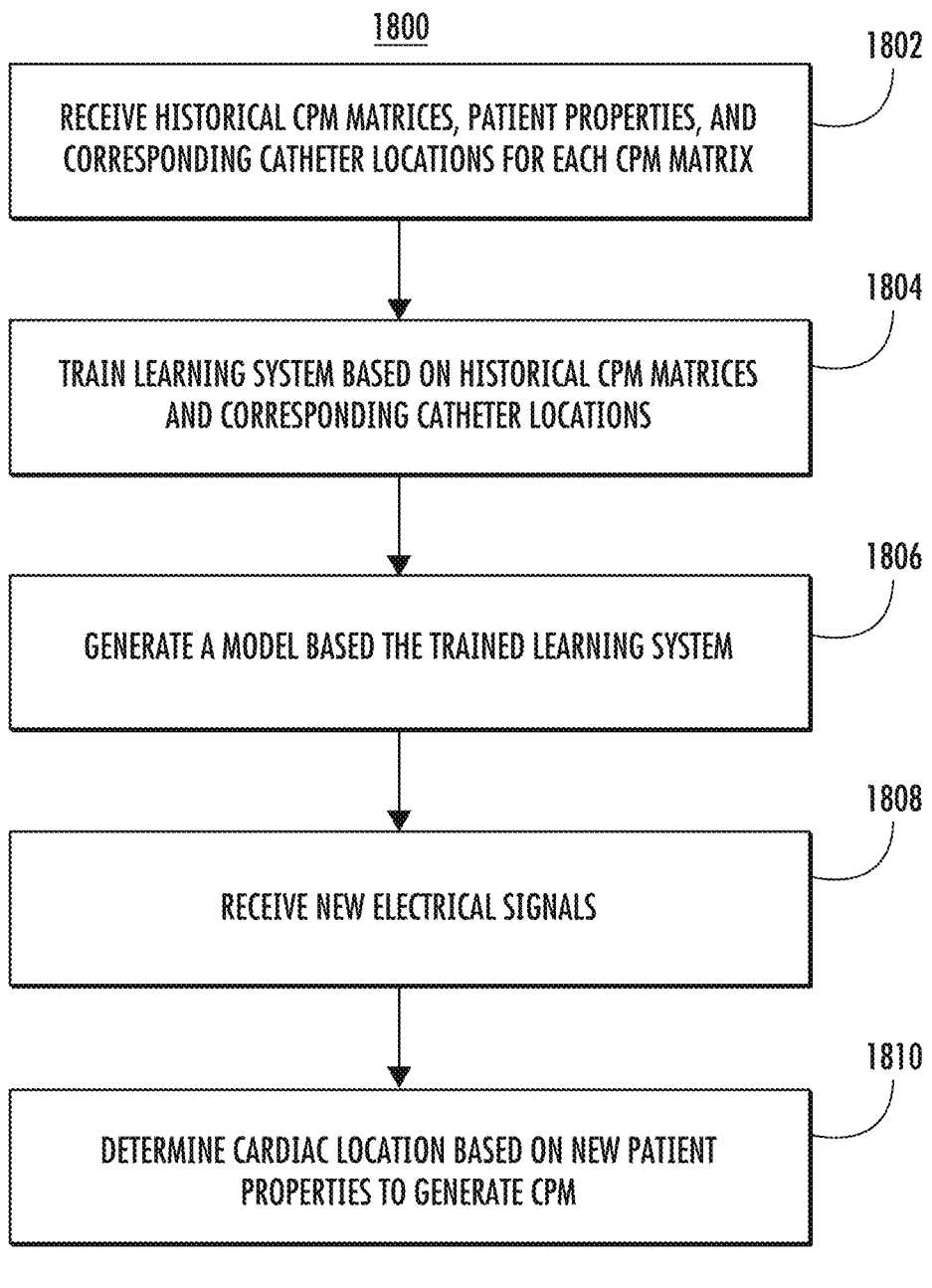

1800

1802
RECEIVE HISTORICAL CPM MATRICES, PATIENT PROPERTIES, AND CORRESPONDING CATHETER LOCATIONS FOR EACH CPM MATRIX

1804
TRAIN LEARNING SYSTEM BASED ON HISTORICAL CPM MATRICES AND CORRESPONDING CATHETER LOCATIONS

1806
GENERATE A MODEL BASED THE TRAINED LEARNING SYSTEM

1808
RECEIVE NEW ELECTRICAL SIGNALS

1810
DETERMINE CARDIAC LOCATION BASED ON NEW PATIENT PROPERTIES TO GENERATE CPM

FIG. 18b

SYSTEM AND METHOD TO DETERMINE THE LOCATION OF A CATHETER

CROSS REFERENCE TO RELATED APPLICATION(S)

This application is a continuation-in-part of U.S. Non-Provisional patent application Ser. No. 17/366,364, filed on Jul. 2, 2021 which claims the benefit of U.S. Provisional Application No. 63/049,191, filed Jul. 8, 2020, which is incorporated by reference as if fully set forth.

FIELD OF INVENTION

The present invention is related to artificial intelligence and machine learning associated with optimizing cardiac mapping including a system and method to determine an improved mapping matrix between patient properties and catheter locations (CPM matrix). Such a matrix can be used to determine the location of a catheter based on new received patient properties.

BACKGROUND

Medical conditions such as cardiac arrhythmia (e.g., atrial fibrillation (AF)) are often diagnosed and treated via intra-body procedures. For example, electrical pulmonary vein isolation (PVI) from the left atrial (LA) body is performed using ablation for treating AF. PVI, and many other minimally invasive catheterizations, require real-time visualization and mapping of an intra-body surface.

Visualization and mapping of intra-body body parts can be performed by mapping propagation of activation waves, Fluoroscopies, computerized tomography (CT) and magnetic resonance imaging (MRI), as well as other techniques which may require a greater than desirable amount of time or resources to provide the visualization and mapping.

SUMMARY

Systems, devices, and techniques are disclosed for generating improved current-to-position (i.e CPM) matrices. The system includes a processor configured to receive a plurality of historical, sparse CPM matrices and a plurality of historical, supplemented CPM matrices, wherein each sparse CPM matrix is associated with a respective supplemented CPM matrix; train a learning system based on the plurality of historical, sparse CPM matrices and the plurality of historical, supplemented CPM matrices, wherein the learning system is trained so as to generate a supplemented CPM matrix given a sparse CPM matrix; receive, by the trained learning system, a new, sparse CPM matrix; and generate, with the trained learning system, a new supplemented CPM matrix.

BRIEF DESCRIPTION OF THE DRAWINGS

A more detailed understanding may be had from the following description, given by way of example in conjunction with the accompanying drawings, wherein like reference numerals in the figures indicate like elements, and wherein:

FIG. 18b is a flowchart for determining catheter locations and generating current to position mappings (CPMs) for multiple locations;

DETAILED DESCRIPTION

According to exemplary embodiments of the disclosed subject matter, new current to position mapping (CPM) matrices may be generated. According to an embodiment of the invention, a new CPM matrix may be generated from a sparse, CPM matrix that is input into a trained learning system, such as a neural network. As further disclosed herein, a CPM is generated based on electrical signals transmitted by a catheter electrode and received at a plurality of body patches on the surface of a patient's body. The electrical signals are correlated based on known location of the catheter, as determined independently using, for example, magnetic fields (e.g., received and/or emitted by a magnetic catheter sensor, location pad, body patches, etc.). However, it is a time and labor-intensive process to generate a comprehensive CPM matrix, as electrical signals and position data need to be acquired across a wide range of locations. Thus, there is provided a system and method for acquiring a supplemented CPM matrix from a given CPM matrix having only sparse data, using a learning system.

It may be understood that a "sparse" CPM matrix refers to a CPM matrix calculated from electrical current data and position data, wherein the electrical current data and position data are acquired at a first number of locations. It may also be understood that a "supplemented" CPM matrix refers to a CPM matrix calculated from electrical current data and position data, wherein the electrical current data and position data are acquired at a second number of locations, the second number of locations being higher than the first number of locations.

For example, if a "supplemented" CPM matrix provides a mapping between electrical current and position data at 1000 distinct points in the heart, a "sparse" CPM matrix may provide a mapping between these parameters at only 100 distinct points in the heart.

It is an object of the present invention to estimate a supplemented CPM matrix based on a given sparse CPM matrix. It is a further object of the invention to use a learning system to determine a relationship between a given sparse CPM matrix and a given supplemented CPM matrix.

The new CPM matrices may be generated such that new CPM data for a plurality of cardiac locations is generated based on only a subset of known electrical signals corresponding to the plurality of cardiac locations. Alternatively, or in addition, a CPM matrix may be generated based on correlations between historical CPM and corresponding known catheter locations. That is, the new CPM data may be generated such that new CPM data for a plurality of cardiac locations is generated without any known catheter locations corresponding to the plurality of catheter locations.

Figure 1:
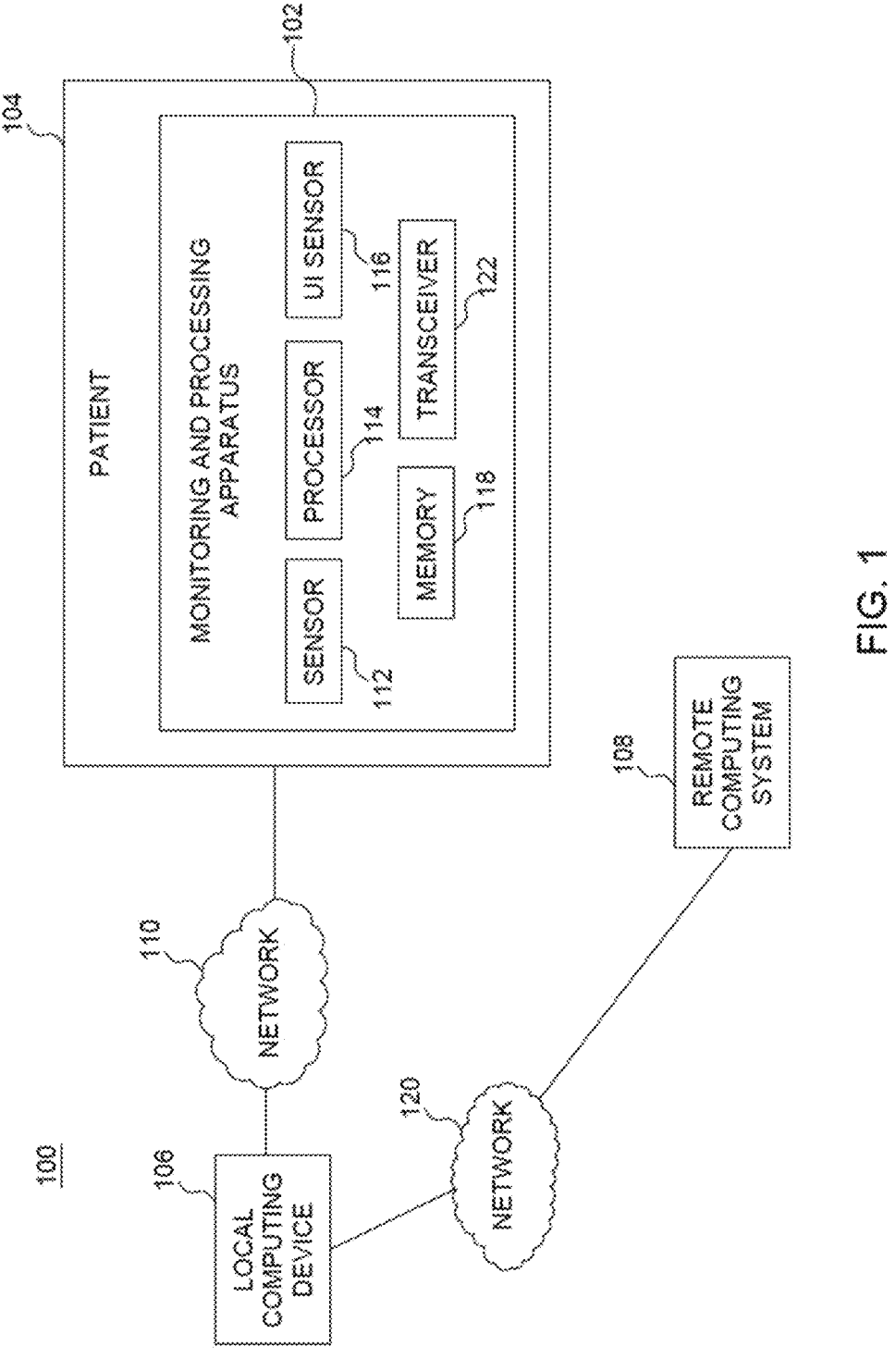
FIG. 1 is a block diagram of an example system for remotely monitoring and communicating patient biometrics.

FIG. 1 is a block diagram of an example system 100 for remotely monitoring and communicating patient biometrics (i.e., patient data). In the example illustrated in FIG. 1, the system 100 includes a patient biometric monitoring and processing apparatus 102 associated with a patient 104, a local computing device 106, a remote computing system 108, a first network 110 and a second network 120.

According to an embodiment, a monitoring and processing apparatus 102 may be an apparatus that is internal to the patient's body (e.g., subcutaneously implantable). The monitoring and processing apparatus 102 may be inserted into a patient via any applicable manner including orally injecting, surgical insertion via a vein or artery, an endoscopic procedure, or a laparoscopic procedure.

According to an embodiment, a monitoring and processing apparatus 102 may be an apparatus that is external to the patient. For example, as described in more detail below, the monitoring and processing apparatus 102 may include an attachable patch (e.g., that attaches to a patient's skin). The monitoring and processing apparatus 102 may also include a catheter with one or more electrodes, a probe, a blood pressure cuff, a weight scale, a bracelet or smart watch biometric tracker, a glucose monitor, a continuous positive airway pressure (CPAP) machine or virtually any device which may provide an input concerning the health or biometrics of the patient.

According to an embodiment, a monitoring and processing apparatus 102 may include both components that are internal to the patient and components that are external to the patient.

A single monitoring and processing apparatus 102 is shown in FIG. 1. Example systems may, however, may include a plurality of patient biometric monitoring and processing apparatuses. A patient biometric monitoring and processing apparatus may be in communication with one or more other patient biometric monitoring and processing apparatuses. Additionally, or alternatively, a patient biometric monitoring and processing apparatus may be in communication with the network 110.

One or more monitoring and processing apparatuses 102 may acquire patient biometric data (e.g., electrical signals, blood pressure, temperature, blood glucose level or other biometric data) and receive at least a portion of the patient biometric data representing the acquired patient biometrics and additional formation associated with acquired patient biometrics from one or more other monitoring and processing apparatuses 102. The additional information may be, for example, diagnosis information and/or additional information obtained from an additional device such as a wearable device. Each monitoring and processing apparatus 102 may process data, including its own acquired patient biometrics as well as data received from one or more other monitoring and processing apparatuses 102.

In FIG. 1, network 110 is an example of a short-range network (e.g., local area network (LAN), or personal area network (PAN)). Information may be sent, via short-range network 110, between monitoring a processing apparatus 102 and local computing device 106 using any one of various short-range wireless communication protocols, such as Bluetooth, Wi-Fi, Zigbee, Z-Wave, near field communications (NFC), ultraband, Zigbee, or infrared (IR).

Network 120 may be a wired network, a wireless network or include one or more wired and wireless networks. For example, a network 120 may be a long-range network (e.g., wide area network (WAN), the internet, or a cellular network). Information may be sent, via network 120 using any one of various long-range wireless communication protocols (e.g., TCP/IP, HTTP, 3G, 4G/LTE, or 5G/New Radio).

The patient monitoring and processing apparatus 102 may include a patient biometric sensor 112, a processor 114, a user input (UI) sensor 116, a memory 118, and a transmitter-receiver (i.e., transceiver) 122. The patient monitoring and processing apparatus 102 may continually or periodically monitor, store, process and communicate, via network 110, any number of various patient biometrics. Examples of patient biometrics include electrical signals (e.g., ECG signals and brain biometrics), blood pressure data, blood glucose data and temperature data. The patient biometrics may be monitored and communicated for treatment across any number of various diseases, such as cardiovascular diseases (e.g., arrhythmias, cardiomyopathy, and coronary artery disease) and autoimmune diseases (e.g., type I and type II diabetes).

Patient biometric sensor 112 may include, for example, one or more sensors configured to sense a type of biometric patient biometrics. For example, patient biometric sensor 112 may include an electrode configured to acquire electrical signals (e.g., heart signals, brain signals or other bioelectrical signals), a temperature sensor, a blood pressure sensor, a blood glucose sensor, a blood oxygen sensor, a pH sensor, an accelerometer and a microphone.

As described in more detail below, patient biometric monitoring and processing apparatus 102 may be an ECG monitor for monitoring ECG signals of a heart. The patient biometric sensor 112 of the ECG monitor may include one or more electrodes for acquiring ECG signals. The ECG signals may be used for treatment of various cardiovascular diseases.

In another example, the patient biometric monitoring and processing apparatus 102 may be a continuous glucose monitor (CGM) for continuously monitoring blood glucose levels of a patient on a continual basis for treatment of various diseases, such as type I and type II diabetes. The CGM may include a subcutaneously disposed electrode, which may monitor blood glucose levels from interstitial fluid of the patient. The CGM may be, for example, a component of a closed-loop system in which the blood glucose data is sent to an insulin pump for calculated delivery of insulin without user intervention.

Transceiver 122 may include a separate transmitter and receiver. Alternatively, transceiver 122 may include a transmitter and receiver integrated into a single device.

Processor 114 may be configured to store patient data, such as patient biometric data in memory 118 acquired by patient biometric sensor 112, and communicate the patient data, across network 110, via a transmitter of transceiver 122. Data from one or more other monitoring and processing apparatus 102 may also be received by a receiver of transceiver 122, as described in more detail below.

According to an embodiment, the monitoring and processing apparatus 102 includes UI sensor 116 which may be, for example, a piezoelectric sensor or a capacitive sensor configured to receive a user input, such as a tapping or touching. For example, UI sensor 116 may be controlled to implement a capacitive coupling, in response to tapping or touching a surface of the monitoring and processing apparatus 102 by the patient 104. Gesture recognition may be implemented via any one of various capacitive types, such as resistive capacitive, surface capacitive, projected capacitive, surface acoustic wave, piezoelectric and infra-red touching. Capacitive sensors may be disposed at a small area or over a length of the surface such that the tapping or touching of the surface activates the monitoring device.

As described in more detail below, the processor 114 may be configured to respond selectively to different tapping patterns of the capacitive sensor (e.g., a single tap or a double tap), which may be the UI sensor 116, such that different tasks of the patch (e.g., acquisition, storing, or transmission of data) may be activated based on the detected pattern. In some embodiments, audible feedback may be given to the user from processing apparatus 102 when a gesture is detected.

The local computing device 106 of system 100 is in communication with the patient biometric monitoring and processing apparatus 102 and may be configured to act as a gateway to the remote computing system 108 through the second network 120. The local computing device 106 may be, for example, a, smart phone, smartwatch, tablet or other portable smart device configured to communicate with other devices via network 120. Alternatively, the local computing device 106 may be a stationary or standalone device, such as a stationary base station including, for example, modem and/or router capability, a desktop or laptop computer using an executable program to communicate information between the processing apparatus 102 and the remote computing system 108 via the PC's radio module, or a USB dongle. Patient biometrics may be communicated between the local computing device 106 and the patient biometric monitoring and processing apparatus 102 using a short-range wireless technology standard (e.g., Bluetooth, Wi-Fi, ZigBee, Z-wave and other short-range wireless standards) via the short-range wireless network 110, such as a local area network (LAN) (e.g., a personal area network (PAN)). In some embodiments, the local computing device 106 may also be configured to display the acquired patient electrical signals and information associated with the acquired patient electrical signals, as described in more detail below.

In some embodiments, remote computing system 108 may be configured to receive at least one of the monitored patient biometrics and information associated with the monitored patient via network 120, which is a long-range network. For example, if the local computing device 106 is a mobile phone, network 120 may be a wireless cellular network, and information may be communicated between the local computing device 106 and the remote computing system 108 via a wireless technology standard, such as any of the wireless technologies mentioned above. As described in more detail below, the remote computing system 108 may be configured to provide (e.g., visually display and/or aurally provide) the at least one of the patient biometrics and the associated information to a healthcare professional (e.g., a physician).

Figure 2:
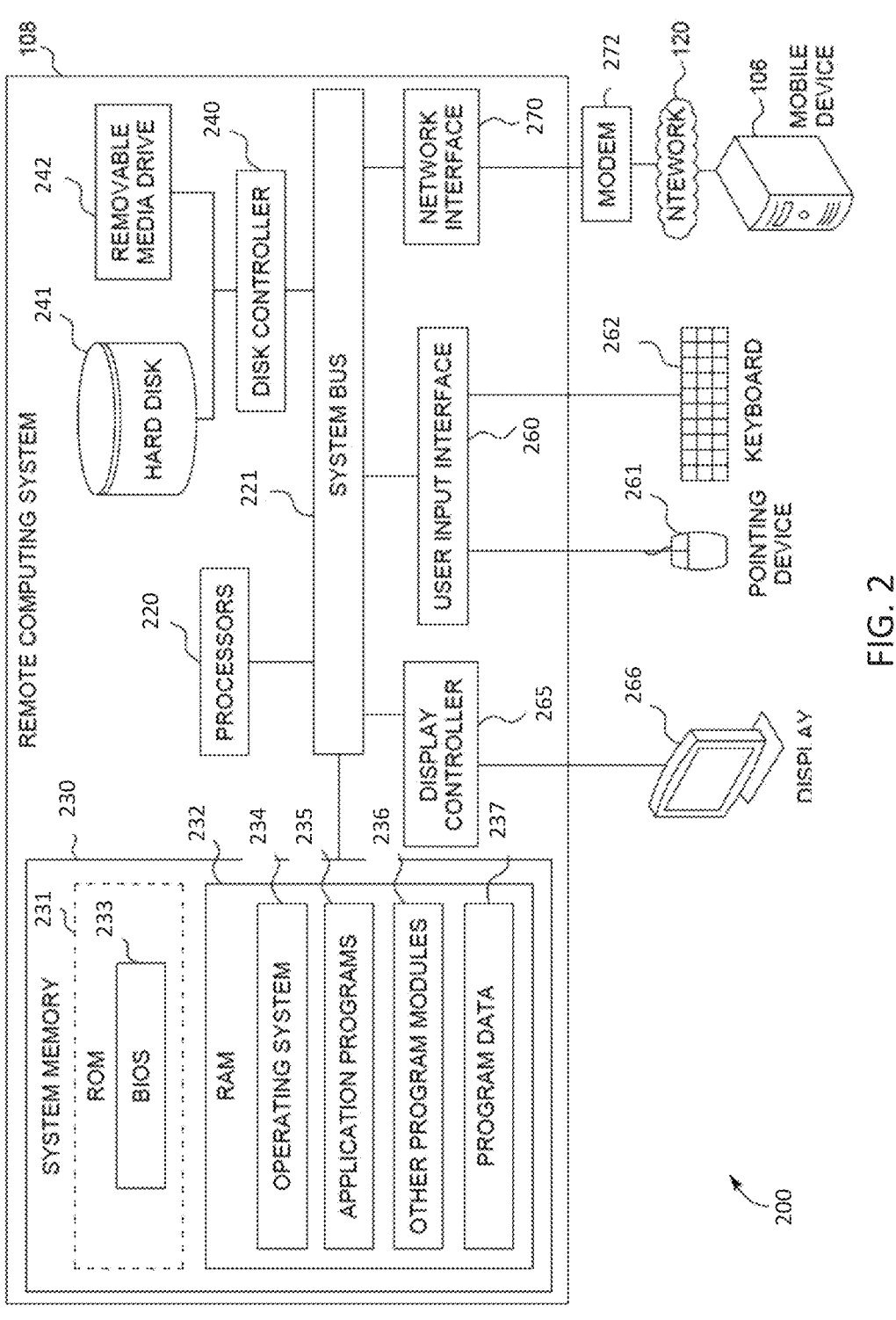
FIG. 2 is a system diagram of an example of a computing environment in communication with network.

FIG. 2 is a system diagram of an example of a computing environment 200 in communication with network 120. In some instances, the computing environment 200 is incorporated in a public cloud computing platform (such as Amazon Web Services or Microsoft Azure), a hybrid cloud computing platform (such as HP Enterprise OneSphere) or a private cloud computing platform.

As shown in FIG. 2, computing environment 200 includes remote computing system 108 (hereinafter computer system), which is one example of a computing system upon which embodiments described herein may be implemented.

The remote computing system 108 may, via processors 220, which may include one or more processors, perform various functions. The functions may include analyzing monitored patient biometrics and the associated information and, according to physician-determined or algorithm driven thresholds and parameters, providing (e.g., via display 266) alerts, additional information or instructions. As described in more detail below, the remote computing system 108 may be used to provide (e.g., via display 266) healthcare personnel (e.g., a physician) with a dashboard of patient information, such that such information may enable healthcare personnel to identify and prioritize patients having more critical needs than others.

As shown in FIG. 2, the computer system 210 may include a communication mechanism such as a bus 221 or other communication mechanism for communicating information within the computer system 210. The computer system 210 further includes one or more processors 220 coupled with the bus 221 for processing the information. The processors 220 may include one or more CPUs, GPUs, or any other processor known in the art.

The computer system 210 also includes a system memory 230 coupled to the bus 221 for storing information and instructions to be executed by processors 220. The system memory 230 may include computer readable storage media in the form of volatile and/or nonvolatile memory, such as read only system memory (ROM) 231 and/or random-access memory (RAM) 232. The system memory RAM 232 may include other dynamic storage device(s) (e.g., dynamic RAM, static RAM, and synchronous DRAM). The system memory ROM 231 may include other static storage device (s) (e.g., programmable ROM, erasable PROM, and electrically erasable PROM). In addition, the system memory 230 may be used for storing temporary variables or other intermediate information during the execution of instructions by the processors 220. A basic input/output system 233 (BIOS) may contain routines to transfer information between elements within computer system 210, such as during start-up, that may be stored in system memory ROM 231. RAM 232 may comprise data and/or program modules that are immediately accessible to and/or presently being operated on by the processors 220. System memory 230 may additionally include, for example, operating system 234, application programs 235, other program modules 236 and program data 237.

The illustrated computer system 210 also includes a disk controller 240 coupled to the bus 221 to control one or more storage devices for storing information and instructions, such as a magnetic hard disk 241 and a removable media drive 242 (e.g., floppy disk drive, compact disc drive, tape drive, and/or solid-state drive). The storage devices may be added to the computer system 210 using an appropriate device interface (e.g., a small computer system interface (SCSI), integrated device electronics (IDE), Universal Serial Bus (USB), or FireWire).

The computer system 210 may also include a display controller 265 coupled to the bus 221 to control a monitor or display 266, such as a cathode ray tube (CRT) or liquid crystal display (LCD), for displaying information to a computer user. The illustrated computer system 210 includes a user input interface 260 and one or more input devices, such as a keyboard 262 and a pointing device 261, for interacting with a computer user and providing information to the processor 220. The pointing device 261, for example, may be a mouse, a trackball, or a pointing stick for communicating direction information and command selections to the processor 220 and for controlling cursor movement on the display 266. The display 266 may provide a touch screen interface that may allow input to supplement or replace the communication of direction information and command selections by the pointing device 261 and/or keyboard 262.

The computer system 210 may perform a portion or each of the functions and methods described herein in response to the processors 220 executing one or more sequences of one or more instructions contained in a memory, such as the system memory 230. Such instructions may be read into the system memory 230 from another computer readable medium, such as a hard disk 241 or a removable media drive 242. The hard disk 241 may contain one or more data stores and data files used by embodiments described herein. Data store contents and data files may be encrypted to improve security. The processors 220 may also be employed in a multi-processing arrangement to execute the one or more sequences of instructions contained in system memory 230. In alternative embodiments, hard-wired circuitry may be used in place of or in combination with software instructions. Thus, embodiments are not limited to any specific combination of hardware circuitry and software.

As stated above, the computer system 210 may include at least one computer readable medium or memory for holding instructions programmed according to embodiments described herein and for containing data structures, tables, records, or other data described herein. The term computer readable medium as used herein refers to any non-transitory, tangible medium that participates in providing instructions to the processor 220 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 241 or removable media drive 242. Non-limiting examples of volatile media include dynamic memory, such as system memory 230. Non-limiting examples of transmission media include coaxial cables, copper wire, and fiber optics, including the wires that make up the bus 221. Transmission media may also take the form of acoustic or light waves, such as those generated during radio wave and infrared data communications.

The computing environment 200 may further include the computer system 210 operating in a networked environment using logical connections to local computing device 106 and one or more other devices, such as a personal computer (laptop or desktop), mobile devices (e.g., patient mobile devices), a server, a router, a network PC, a peer device or other common network node, and typically includes many or all of the elements described above relative to computer system 210. When used in a networking environment, computer system 210 may include modem 272 for establishing communications over a network 120, such as the Internet. Modem 272 may be connected to system bus 221 via network interface 270, or via another appropriate mechanism.

Network 120, as shown in FIGS. 1 and 2, may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 610 and other computers (e.g., local computing device 106).

Figure 3:
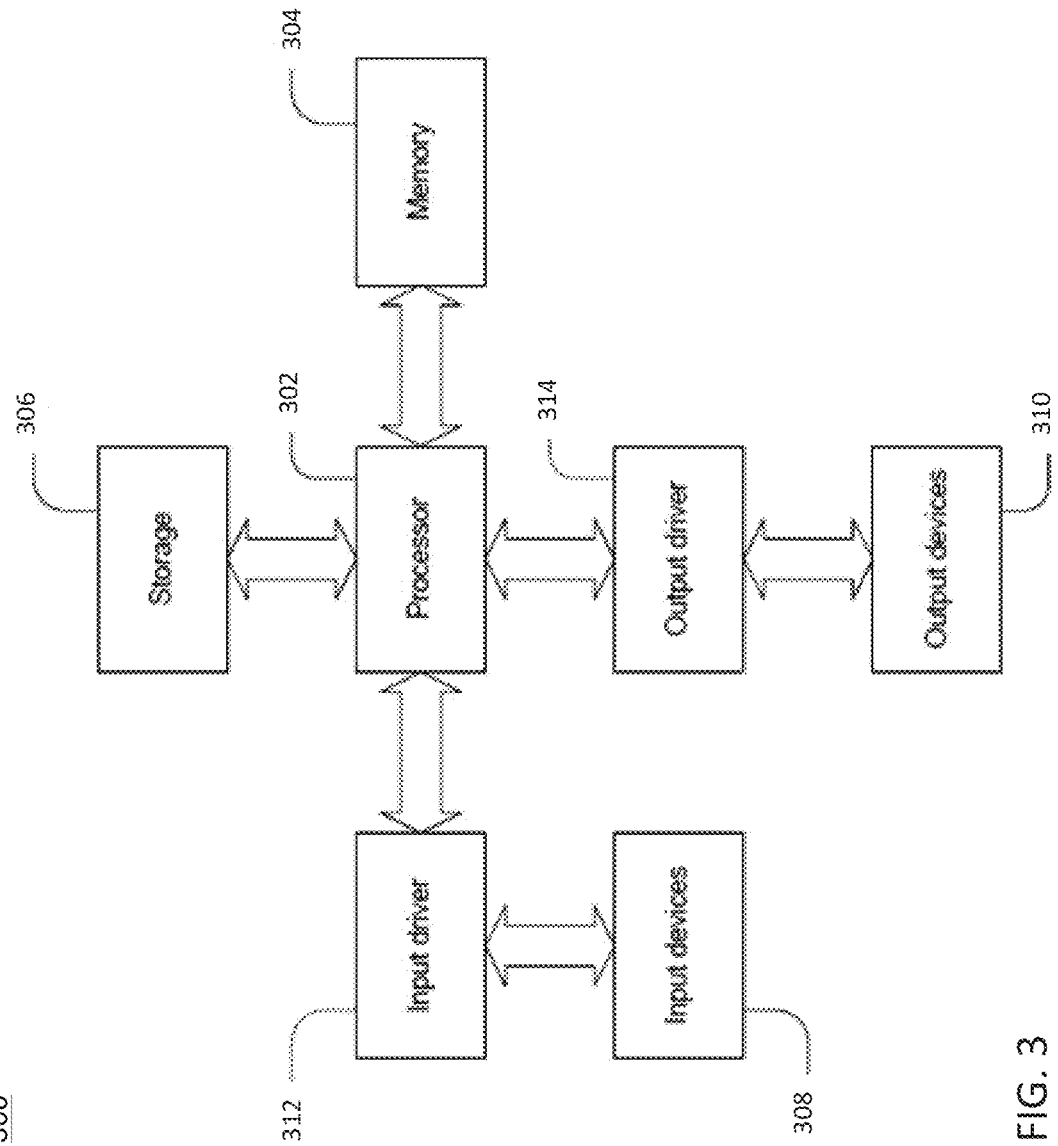
FIG. 3 is a block diagram of an example device in which one or more features of the disclosure can be implemented.

FIG. 3 is a block diagram of an example device 300 in which one or more features of the disclosure can be implemented. The device 300 may be local computing device 106, for example. The device 300 can include, for example, a computer, a gaming device, a handheld device, a set-top box, a television, a mobile phone, or a tablet computer. The device 300 includes a processor 302, a memory 304, a storage device 306, one or more input devices 308, and one or more output devices 310. The device 300 can also optionally include an input driver 312 and an output driver 314. It is understood that the device 300 can include additional components not shown in FIG. 3 including an artificial intelligence accelerator.

In various alternatives, the processor 302 includes a central processing unit (CPU), a graphics processing unit (GPU), a CPU and GPU located on the same die, or one or more processor cores, wherein each processor core can be a CPU or a GPU. In various alternatives, the memory 304 is located on the same die as the processor 302, or is located separately from the processor 302. The memory 304 includes a volatile or non-volatile memory, for example, random access memory (RAM), dynamic RAM, or a cache.

The storage device 306 includes a fixed or removable storage means, for example, a hard disk drive, a solid-state drive, an optical disk, or a flash drive. The input devices 308 include, without limitation, a keyboard, a keypad, a touch screen, a touch pad, a detector, a microphone, an accelerometer, a gyroscope, a biometric scanner, or a network connection (e.g., a wireless local area network card for transmission and/or reception of wireless IEEE 802 signals). The output devices 310 include, without limitation, a display, a speaker, a printer, a haptic feedback device, one or more lights, an antenna, or a network connection (e.g., a wireless local area network card for transmission and/or reception of wireless IEEE 802 signals).

The input driver 312 communicates with the processor 302 and the input devices 308, and permits the processor 302 to receive input from the input devices 308. The output driver 314 communicates with the processor 302 and the output devices 310, and permits the processor 302 to send output to the output devices 310. It is noted that the input driver 312 and the output driver 314 are optional components, and that the device 300 will operate in the same manner if the input driver 312 and the output driver 314 are not present. The output driver 316 includes an accelerated processing device ("APD") 316 which is coupled to a display device 318. The APD accepts compute commands and graphics rendering commands from processor 302, processes those compute and graphics rendering commands, and provides pixel output to display device 318 for display. As described in further detail below, the APD 316 includes one or more parallel processing units to perform computations in accordance with a single-instruction-multiple-data ("SIMD") paradigm. Thus, although various functionality is described herein as being performed by or in conjunction with the APD 316, in various alternatives, the functionality described as being performed by the APD 316 is additionally or alternatively performed by other computing devices having similar capabilities that are not driven by a host processor (e.g., processor 302) and provides graphical output to a display device 318. For example, it is contemplated that any processing system that performs processing tasks in accordance with a SIMD paradigm may perform the functionality described herein. Alternatively, it is contemplated that computing systems that do not perform processing tasks in accordance with a SIMD paradigm performs the functionality described herein.

Figure 4:
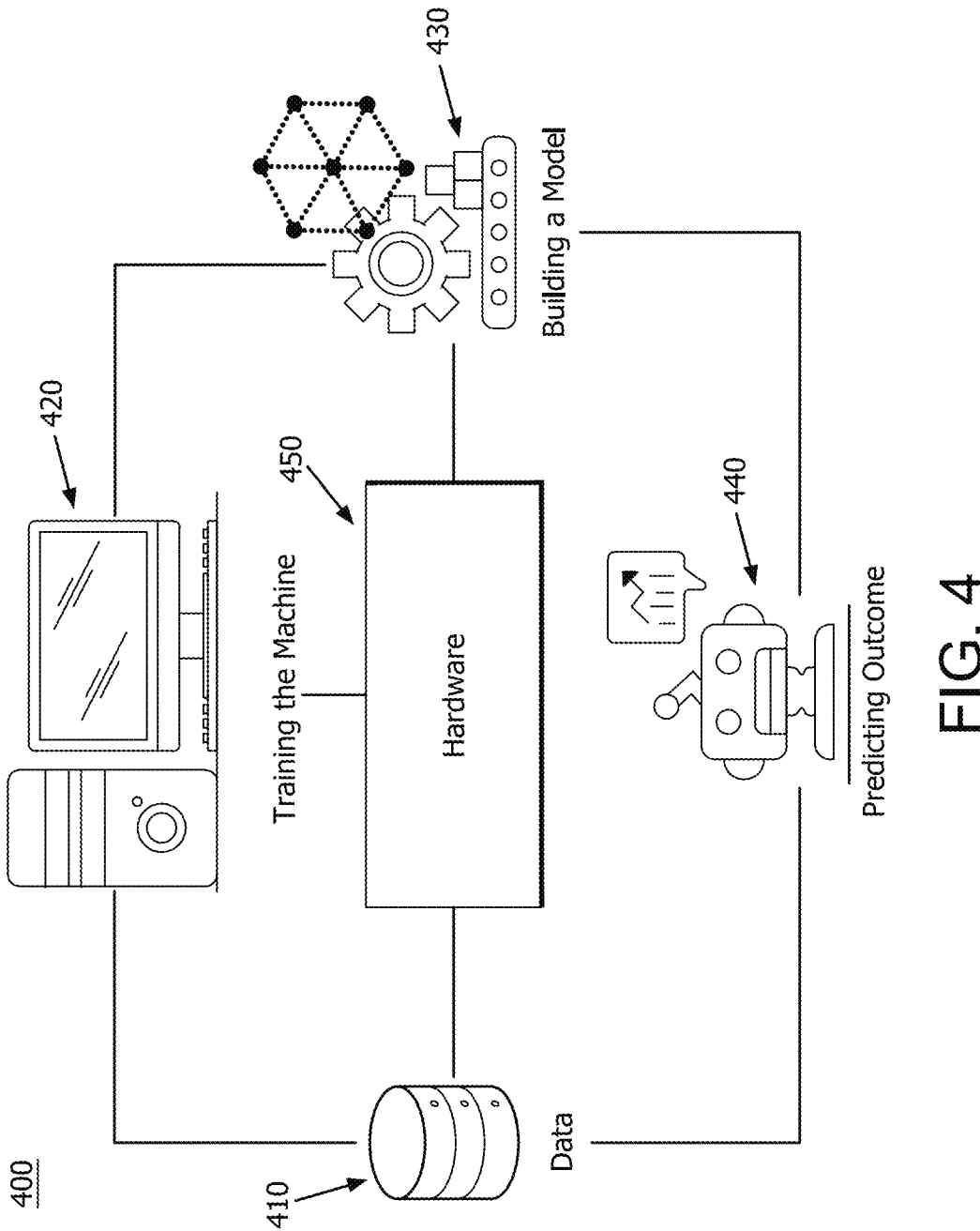
FIG. 4 illustrates a graphical depiction of an artificial intelligence system incorporating the example device of FIG. 3.

FIG. 4 illustrates a graphical depiction of an artificial intelligence system 200 incorporating the example device of FIG. 3. System 400 includes data 410, a machine 420, a model 430, a plurality of outcomes 440 and underlying hardware 450. System 400 operates by using the data 410 to train the machine 420 while building a model 430 to enable a plurality of outcomes 440 to be predicted. The system 400 may operate with respect to hardware 450. In such a configuration, the data 410 may be related to hardware 450 and may originate with apparatus 102, for example. For example, the data 410 may be on-going data, or output data associated with hardware 450. The machine 420 may operate as the controller or data collection associated with the hardware 450, or be associated therewith. The model 430 may be configured to model the operation of hardware 450 and model the data 410 collected from hardware 450 in order to predict the outcome achieved by hardware 450. Using the outcome 440 that is predicted, hardware 450 may be configured to provide a certain desired outcome 440 from hardware 450.

Figure 5:
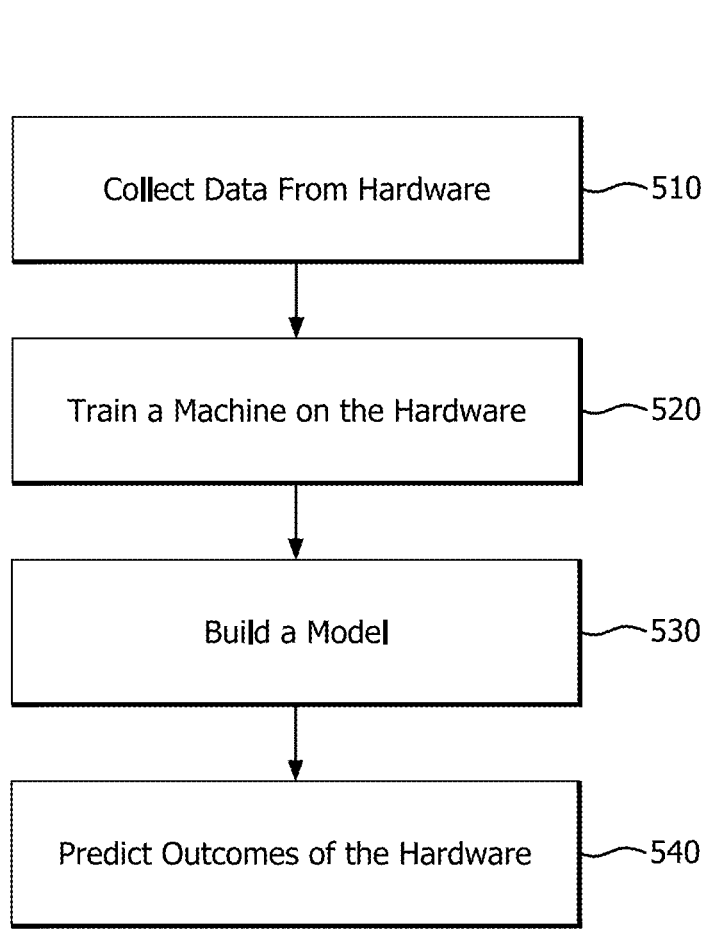
FIG. 5 illustrates a method performed in the artificial intelligence system of FIG. 4.

FIG. 5 illustrates a method 500 performed in the artificial intelligence system of FIG. 4. Method 500 includes collecting data from the hardware at step 510. This data may include currently collected, historical or other data from the hardware. For example, this data may include measurements during a surgical procedure and may be associated with the outcome of the procedure. For example, the temperature of a heart may be collected and correlated with the outcome of a heart procedure.

At step 520, method 500 includes training a machine on the hardware. The training may include an analysis and correlation of the data collected in step 510. For example, in the case of the heart, the data of temperature and outcome may be trained to determine if a correlation or link exists between the temperature of the heart during the procedure and the outcome.

At step 530, method 500 includes building a model on the data associated with the hardware. Building a model may include physical hardware or software modeling, algorithmic modeling and the like, as will be described below. This modeling may seek to represent the data that has been collected and trained.

At step 540, method 500 includes predicting the outcomes of the model associated with the hardware. This prediction of the outcome may be based on the trained model. For example, in the case of the heart, if the temperature during the procedure between 97.7-100.2 produces a positive result from the procedure, the outcome can be predicted in a given procedure based on the temperature of the heart during the procedure. While this model is rudimentary, it is provided for exemplary purposes and to increase understanding of the present invention.

The present system and method operate to train the machine, build the model and predict outcomes using algorithms. These algorithms may be used to solve the trained model and predict outcomes associated with the hardware. These algorithms may be divided generally into classification, regression and clustering algorithms.

For example, a classification algorithm is used in the situation where the dependent variable, which is the variable being predicted, is divided into classes and predicting a class, the dependent variable, for a given input. Thus, a classification algorithm is used to predict an outcome, from a set number of fixed, predefined outcomes. A classification algorithm may include naive Bayes algorithms, decision trees, random forest classifiers, logistic regressions, support vector machines and k nearest neighbors.

Generally, a naive Bayes algorithm follows the Bayes theorem, and follows a probabilistic approach. As would be understood, other probabilistic-based algorithms may also be used, and generally operate using similar probabilistic principles to those described below for the exemplary naive Bayes algorithm.

Figure 6:
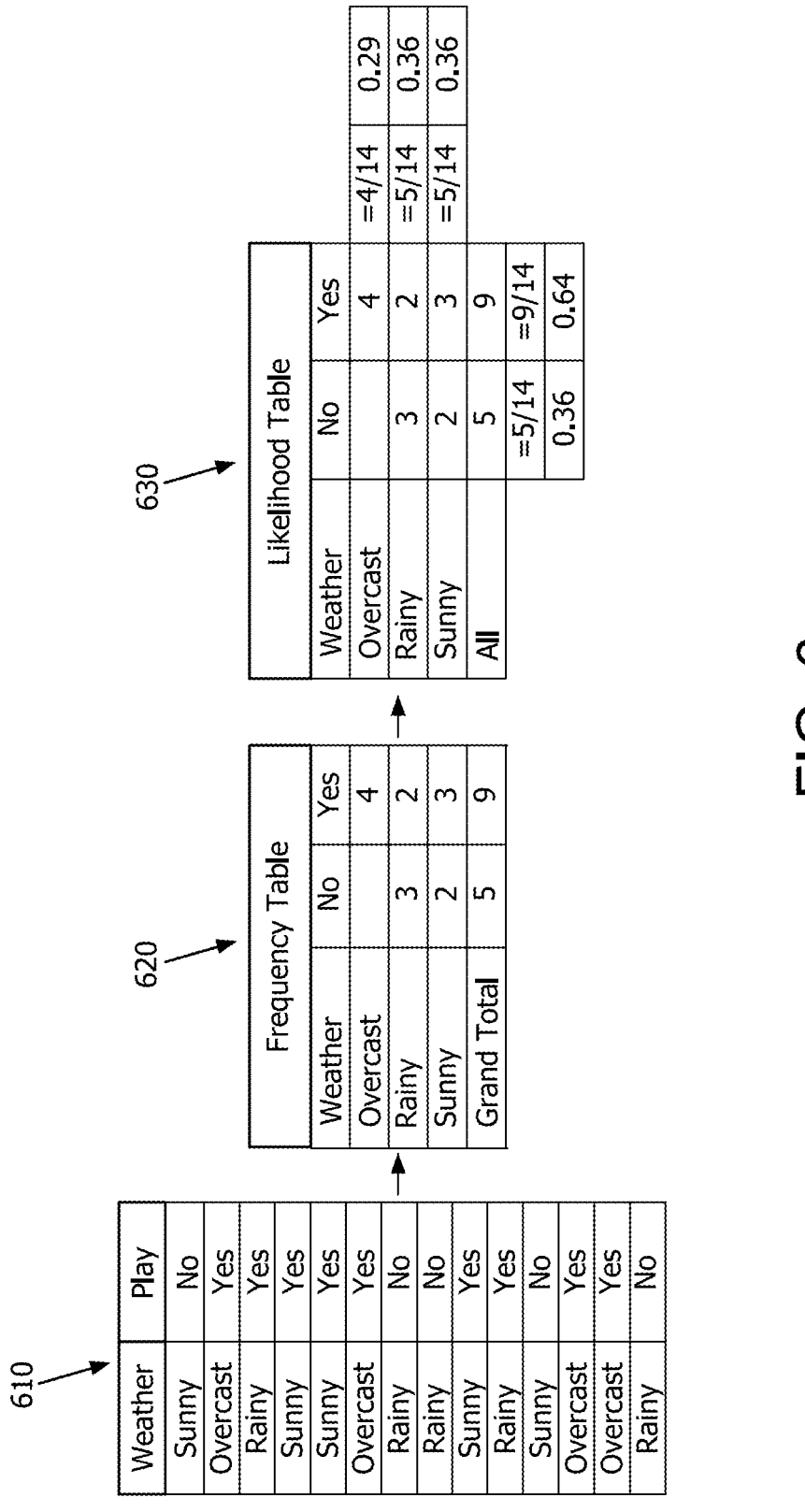
FIG. 6 illustrates an example of the probabilities of a naive Bayes calculation.

FIG. 6 illustrates an example of the probabilities of a naive Bayes calculation. The probability approach of Bayes theorem essentially means, that instead of jumping straight into the data, the algorithm has a set of prior probabilities for each of the classes for the target. After the data is entered, the naive Bayes algorithm may update the prior probabilities to form a posterior probability. This is given by the formula:

$$posterior = \frac{prior \times likelihood}{evidence}$$

This naive Bayes algorithm, and Bayes algorithms generally, may be useful when needing to predict whether your input belongs to a given list of n classes or not. The probabilistic approach may be used because the probabilities for all the n classes will be quite low.

For example, as illustrated in FIG. 6, a person playing golf, which depends on factors including the weather outside shown in a first data set 610. The first data set 610 illustrates the weather in a first column and an outcome of playing associated with that weather in a second column. In the frequency table 620 the frequencies with which certain events occur are generated. In frequency table 620, the frequency of a person playing or not playing golf in each of the weather conditions is determined. From there, a likelihood table is compiled to generate initial probabilities. For example, the probability of the weather being overcast is 0.29 while the general probability of playing is 0.64.

The posterior probabilities may be generated from the likelihood table 630. These posterior probabilities may be configured to answer questions about weather conditions and whether golf is played in those weather conditions. For example, the probability of it being sunny outside and golf being played may be set forth by the Bayesian formula:

$$P(Yes|Sunny)=P(Sunny|Yes)*P(Yes)/P(Sunny)$$

According to likelihood table 630:

$$P(Sunny|Yes)=3/9=0.33,$$

$$P(Sunny)=5/14=0.36,$$

$$P(Yes)=9/14=0.64.$$

Therefore, the P(Yes|Sunny)=0.33*0.64/0.36 or approximately 0.60 (60%).

Generally, a decision tree is a flowchart-like tree structure where each external node denotes a test on an attribute and each branch represents the outcome of that test. The leaf nodes contain the actual predicted labels. The decision tree begins from the root of the tree with attribute values being compared until a leaf node is reached. A decision tree can be used as a classifier when handling high dimensional data and when little time has been spent behind data preparation. Decision trees may take the form of a simple decision tree, a linear decision tree, an algebraic decision tree, a deterministic decision tree, a randomized decision tree, a nondeterministic decision tree, and a quantum decision tree. An exemplary decision tree is provided below in FIG. 7.

Figure 7:
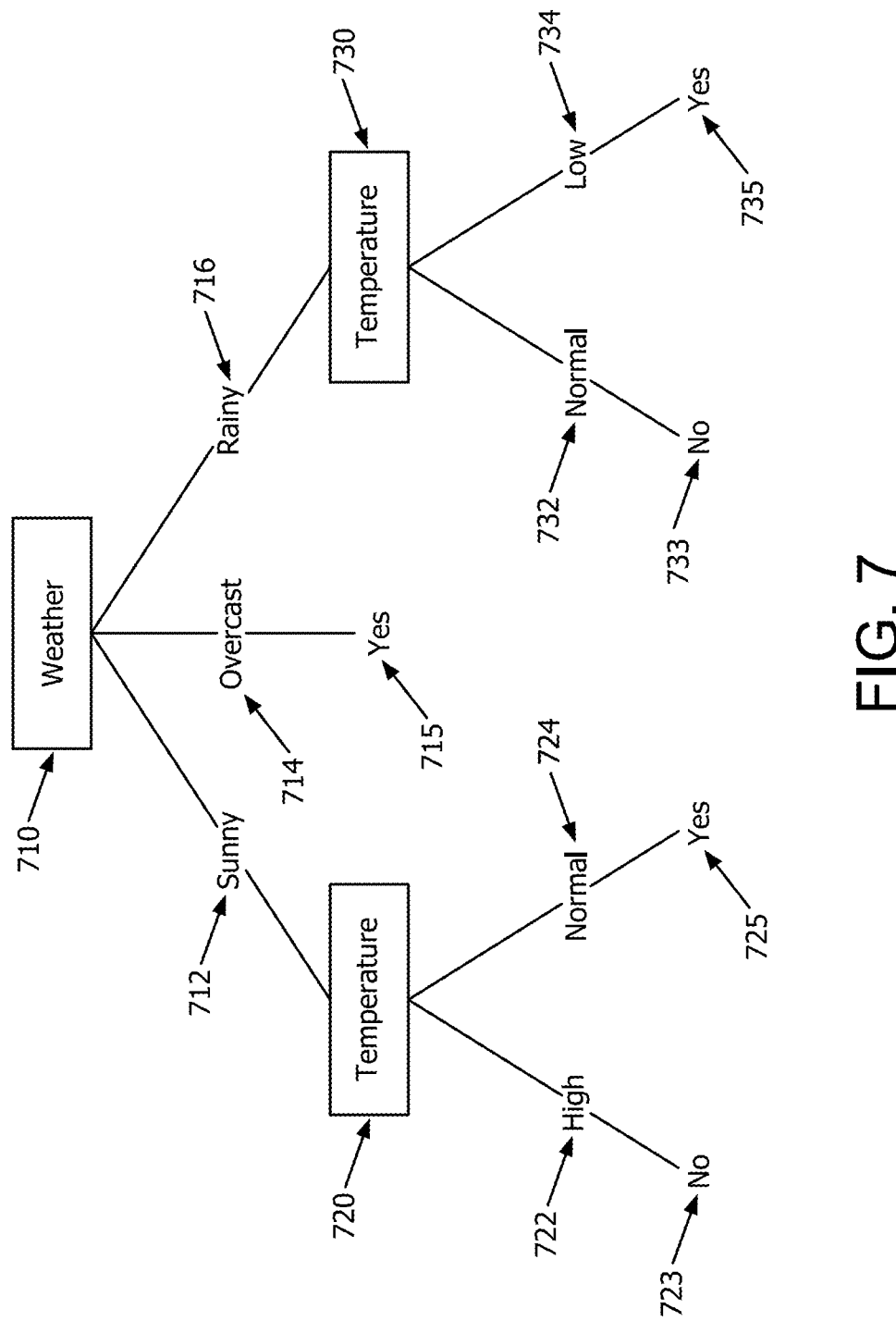
FIG. 7 illustrates an exemplary decision tree.

FIG. 7 illustrates a decision tree, along the same structure as the Bayes example above, in deciding whether to play golf. In the decision tree, the first node 710 examines the weather providing sunny 712, overcast 714, and rain 716 as the choices to progress down the decision tree. If the weather is sunny, the leg of the tree is followed to a second node 720 examining the temperature. The temperature at node 720 may be high 722 or normal 724, in this example. If the temperature at node 720 is high 722, then the predicted outcome of "No" 723 golf occurs. If the temperature at node 720 is normal 724, then the predicted outcome of "Yes" 725 golf occurs.

Further, from the first node 710, an outcome overcast 714, "Yes" 715 golf occurs.

From the first node weather 710, an outcome of rain 716 results in the third node 730 (again) examining temperature. If the temperature at third node 730 is normal 732, then "Yes" 733 golf is played. If the temperature at third node 730 is low 734, then "No" 735 golf is played.

From this decision tree, a golfer plays golf if the weather is overcast 715, in normal temperature sunny weather 725, and in normal temperature rainy weather 733, while the golfer does not play if there is sunny high temperatures 723 or low rainy temperatures 735.

A random forest classifier is a committee of decision trees, where each decision tree has been fed a subset of the attributes of data and predicts on the basis of that subset. The mode of the actual predicted values of the decision trees are considered to provide an ultimate random forest answer. The random forest classifier, generally, alleviates overfitting, which is present in a standalone decision tree, leading to a much more robust and accurate classifier.

Figure 8:
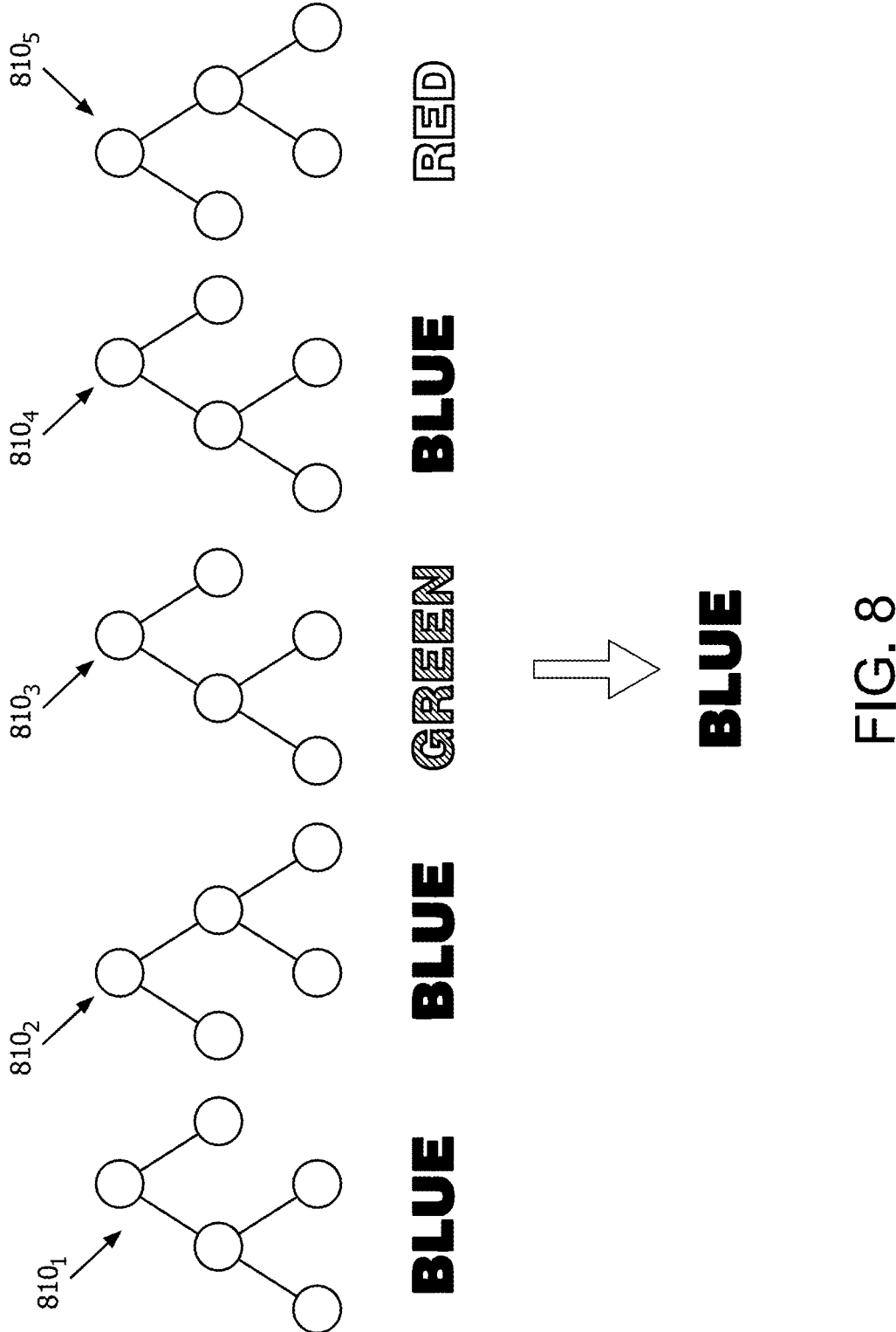
FIG. 8 illustrates an exemplary random forest classifier.

FIG. 8 illustrates an exemplary random forest classifier for classifying the color of a garment. As illustrated in FIG. 8, the random forest classifier includes five decision trees 8101, 8102, 8103, 8104, and 8105 (collectively or generally referred to as decision trees 810). Each of the trees is designed to classify the color of the garment. A discussion of each of the trees and decisions made is not provided, as each individual tree generally operates as the decision tree of FIG. 7. In the illustration, three (8101, 8102, 8104) of the five trees determines that the garment is blue, while one determines the garment is green (8103) and the remaining tree determines the garment is red (8105). The random forest takes these actual predicted values of the five trees and calculates the mode of the actual predicted values to provide random forest answer that the garment is blue.

Logistic Regression is another algorithm for binary classification tasks. Logistic regression is based on the logistic function, also called the sigmoid function. This S-shaped curve can take any real-valued number and map it between 0 and 1 asymptotically approaching those limits. The logistic model may be used to model the probability of a certain class or event existing such as pass/fail, win/lose, alive/dead or healthy/sick. This can be extended to model several classes of events such as determining whether an image contains a cat, dog, lion, etc. Each object being detected in the image would be assigned a probability between 0 and 1 with the sum of the probabilities adding to one.

In the logistic model, the log-odds (the logarithm of the odds) for the value labeled "1" is a linear combination of one or more independent variables ("predictors"); the independent variables can each be a binary variable (two classes, coded by an indicator variable) or a continuous variable (any real value). The corresponding probability of the value labeled "1" can vary between 0 (certainly the value "0") and 1 (certainly the value "1"), hence the labeling; the function that converts log-odds to probability is the logistic function, hence the name. The unit of measurement for the log-odds scale is called a logit, from logistic unit, hence the alternative names. Analogous models with a different sigmoid function instead of the logistic function can also be used, such as the probit model; the defining characteristic of the logistic model is that increasing one of the independent variables multiplicatively scales the odds of the given outcome at a constant rate, with each independent variable having its own parameter; for a binary dependent variable this generalizes the odds ratio.

In a binary logistic regression model, the dependent variable has two levels (categorical). Outputs with more than two values are modeled by multinomial logistic regression and, if the multiple categories are ordered, by ordinal logistic regression (for example the proportional odds ordinal logistic model). The logistic regression model itself simply models probability of output in terms of input and does not perform statistical classification (it is not a classifier), though it can be used to make a classifier, for instance by choosing a cutoff value and classifying inputs with probability greater than the cutoff as one class, below the cutoff as the other; this is a common way to make a binary classifier.

Figure 9:
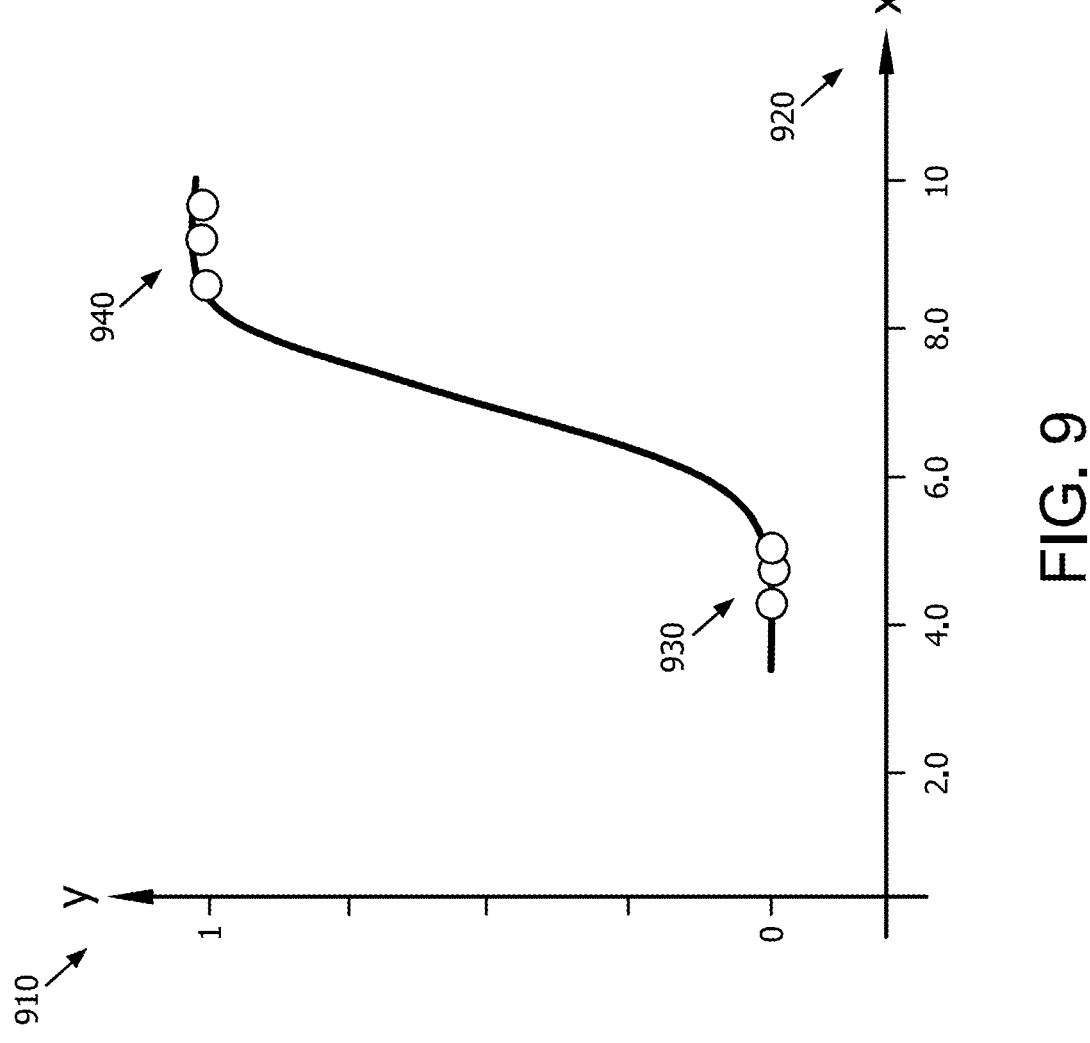
FIG. 9 illustrates an exemplary logistic regression.

FIG. 9 illustrates an exemplary logistic regression. This exemplary logistic regression enables the prediction of an outcome based on a set of variables. For example, based on a person's grade point average, and outcome of being accepted to a school may be predicted. The past history of grade point averages and the relationship with acceptance enables the prediction to occur. The logistic regression of FIG. 9 enables the analysis of the grade point average variable 920 to predict the outcome 910 defined by 0 to 1. At the low end 930 of the S-shaped curve, the grade point average 920 predicts an outcome 910 of not being accepted. While at the high end 940 of the S-shaped curve, the grade point average 920 predicts an outcome 910 of being accepted. Logistic regression may be used to predict house values, customer lifetime value in the insurance sector, etc.

A support vector machine (SVM) may be used to sort the data with the margins between two classes as far apart as possible. This is called maximum margin separation. The SVM may account for the support vectors while plotting the hyperplane, unlike linear regression which uses the entire dataset for that purpose.

Figure 10:
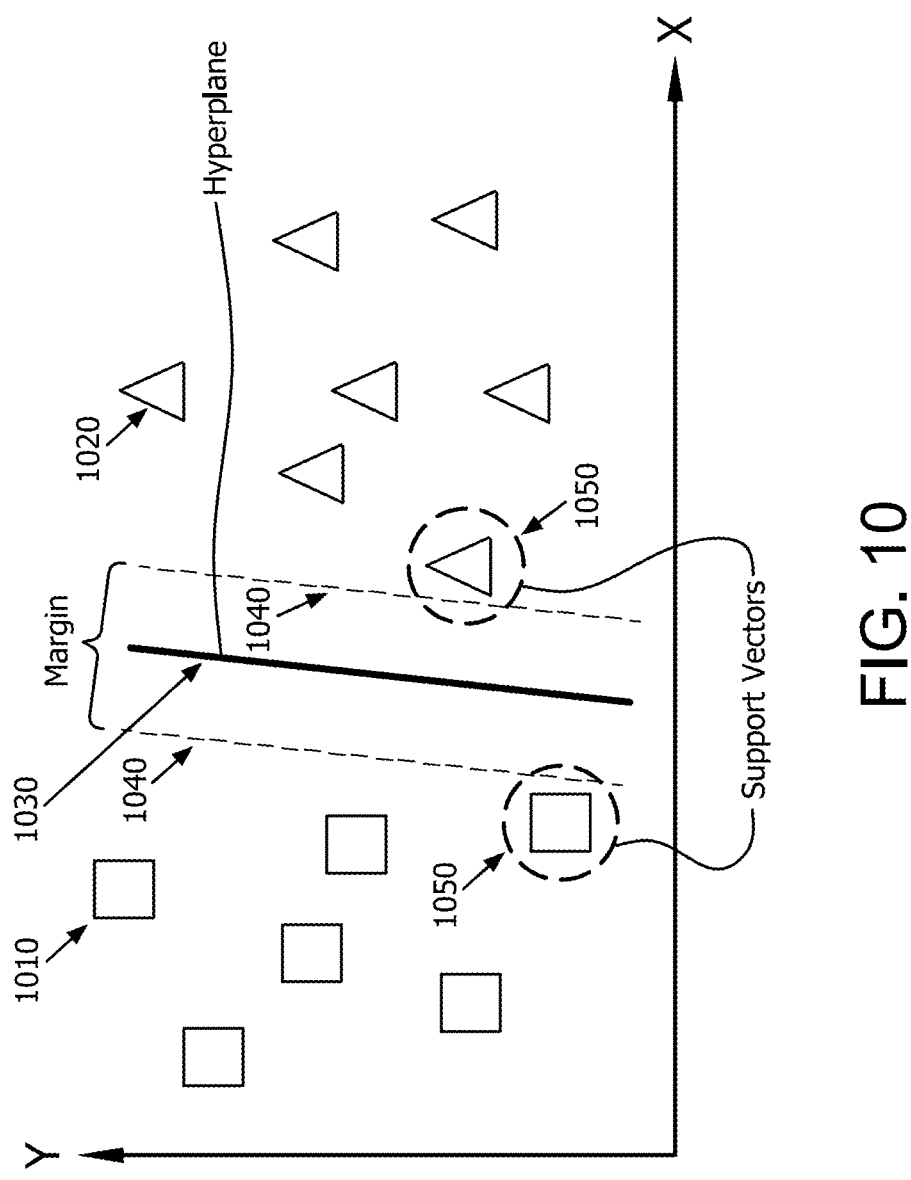
FIG. 10 illustrates an exemplary support vector machine.

FIG. 10 illustrates an exemplary support vector machine. In the exemplary SVM 1000, data may be classified into two different classes represented as squares 1010 and triangles 1020. SVM 1000 operates by drawing a random hyperplane 1030. This hyperplane 1030 is monitored by comparing the distance (illustrated with lines 1040) between the hyperplane 1030 and the closest data points 1050 from each class. The closest data points 1050 to the hyperplane 1030 are known as support vectors. The hyperplane 1030 is drawn based on these support vectors 1050 and an optimum hyperplane has a maximum distance from each of the support vectors 1050.

The distance between the hyperplane 1030 and the support vectors 1050 is known as the margin.

SVM 1000 may be used to classify data by using a hyperplane 1030, such that the distance between the hyperplane 1030 and the support vectors 1050 is maximum. Such an SVM 1000 may be used to predict heart disease, for example.

K Nearest Neighbors (KNN) refers to a set of algorithms that generally do not make assumptions on the underlying data distribution, and perform a reasonably short training phase. Generally, KNN uses many data points separated into several classes to predict the classification of a new sample point. Operationally, KNN specifies an integer N with a new sample. The N entries in the model of the system closest to the new sample are selected. The most common classification of these entries is determined and that classification is assigned to the new sample. KNN generally requires the storage space to increase as the training set increases. This also means that the estimation time increases in proportion to the number of training points.

In regression algorithms, the output is a continuous quantity so regression algorithms may be used in cases where the target variable is a continuous variable. Linear regression is a general example of regression algorithms. Linear regression may be used to gauge genuine qualities (cost of houses, number of calls, all out deals and so forth) in view of the consistent variable(s). A connection between the variables and the outcome is created by fitting the best line (hence linear regression). This best fit line is known as regression line and spoken to by a direct condition Y=a*X+b. Linear regression is best used in approaches involving a low number of dimensions.

Figure 11:
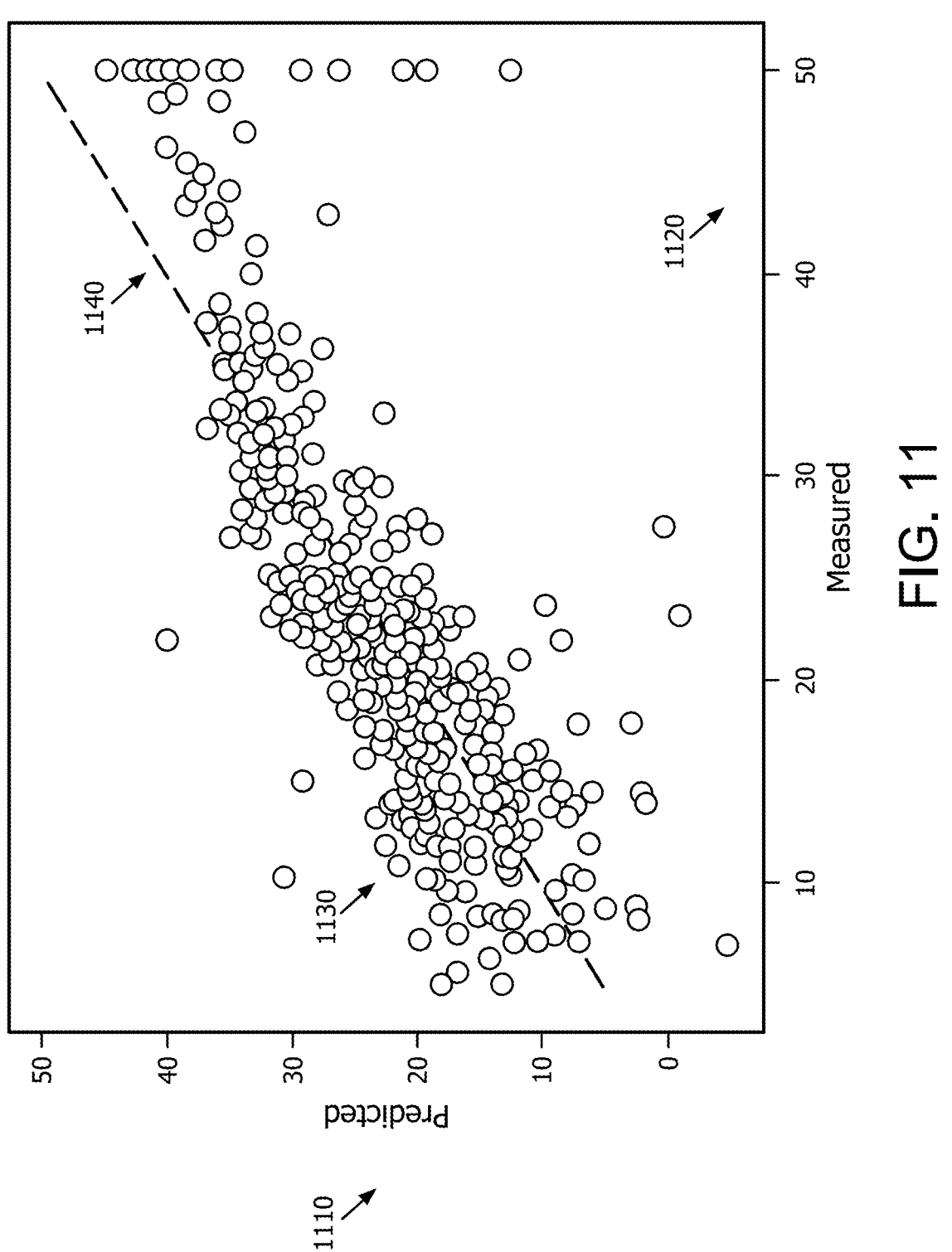
FIG. 11 illustrated an exemplary linear regression model.

FIG. 11 illustrates an exemplary linear regression model. In this model, a predicted variable 1110 is modeled against a measured variable 1120. A cluster of instances of the predicted variable 1110 and measured variable 1120 are plotted as data points 1130. Data points 1130 are then fit with the best fit line 1140. Then the best fit line 1140 is used in subsequent predicted, given a measured variable 1120, the line 1140 is used to predict the predicted variable 1110 for that instance. Linear regression may be used to model and predict in a financial portfolio, salary forecasting, real estate and in traffic in arriving at estimated time of arrival.

Clustering algorithms may also be used to model and train on a data set. In clustering, the input is assigned into two or more clusters based on feature similarity. Clustering algorithms generally learn the patterns and useful insights from data without any guidance. For example, clustering viewers into similar groups based on their interests, age, geography, etc. may be performed using unsupervised learning algorithms like K-means clustering.

K-means clustering generally is regarded as a simple unsupervised learning approach. In K-means clustering similar data points may be gathered together and bound in the form of a cluster. One method for binding the data points together is by calculating the centroid of the group of data points. In determining effective clusters, in K-means clustering the distance between each point from the centroid of the cluster is evaluated. Depending on the distance between the data point and the centroid, the data is assigned to the closest cluster. The goal of clustering is to determine the intrinsic grouping in a set of unlabeled data. The 'K' in K-means stands for the number of clusters formed. The number of clusters (basically the number of classes in which new instances of data may be classified) may be determined by the user. This determination may be performed using feedback and viewing the size of the clusters during training, for example.

K-means is used majorly in cases where the data set has points which are distinct and well separated, otherwise, if the clusters are not separated the modeling may render the clusters inaccurate. Also, K-means may be avoided in cases where the data set contains a high number of outliers or the data set is non-linear.

Figure 12:
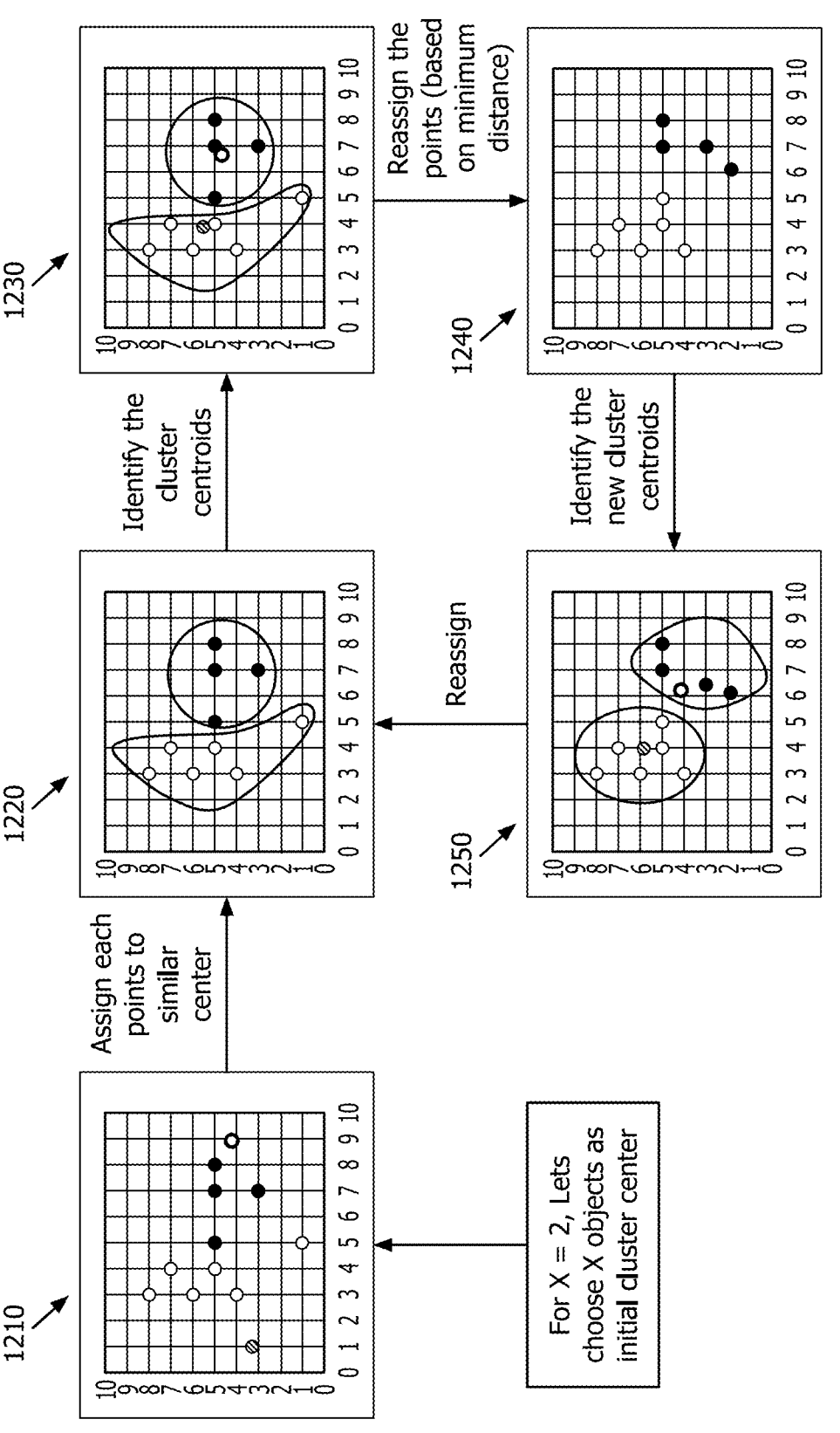
FIG. 12 illustrates an exemplary K-means clustering.

FIG. 12 illustrates a K-means clustering. In K-means clustering, the data points are plotted and the K value is assigned. For example, for K=2 in FIG. 12, the data points are plotted as shown in depiction 1210. The points are then assigned to similar centers at step 1220. The cluster centroids are identified as shown in 1230. Once centroids are identified, the points are reassigned to the cluster to provide the minimum distance between the data point to the respective cluster centroid as illustrated in 1240. Then a new centroid of the cluster may be determined as illustrated in depiction 1250. As the data points are reassigned to a cluster, new cluster centroids formed, an iteration, or series of iterations, may occur to enable the clusters to be minimized in size and the centroid of the optimal centroid determined. Then as new data points are measured, the new data points may be compared with the centroid and cluster to identify with that cluster.

Ensemble learning algorithms may be used. These algorithms use multiple learning algorithms to obtain better predictive performance than could be obtained from any of the constituent learning algorithms alone. Ensemble learning algorithms perform the task of searching through a hypothesis space to find a suitable hypothesis that will make good predictions with a particular problem. Even if the hypothesis space contains hypotheses that are very well-suited for a particular problem, it may be very difficult to find a good hypothesis. Ensemble algorithms combine multiple hypotheses to form a better hypothesis. The term ensemble is usually reserved for methods that generate multiple hypotheses using the same base learner. The broader term of multiple classifier systems also covers hybridization of hypotheses that are not induced by the same base learner.

Evaluating the prediction of an ensemble typically requires more computation than evaluating the prediction of a single model, so ensembles may be thought of as a way to compensate for poor learning algorithms by performing a lot of extra computation. Fast algorithms such as decision trees are commonly used in ensemble methods, for example, random forests, although slower algorithms can benefit from ensemble techniques as well.

An ensemble is itself a supervised learning algorithm, because it can be trained and then used to make predictions. The trained ensemble, therefore, represents a single hypothesis. This hypothesis, however, is not necessarily contained within the hypothesis space of the models from which it is built. Thus, ensembles can be shown to have more flexibility in the functions they can represent. This flexibility can, in theory, enable them to over-fit the training data more than a single model would, but in practice, some ensemble techniques (especially bagging) tend to reduce problems related to over-fitting of the training data.

Empirically, ensemble algorithms tend to yield better results when there is a significant diversity among the models. Many ensemble methods, therefore, seek to promote diversity among the models they combine. Although non-intuitive, more random algorithms (like random decision trees) can be used to produce a stronger ensemble than very deliberate algorithms (like entropy-reducing decision trees). Using a variety of strong learning algorithms, however, has been shown to be more effective than using techniques that attempt to dumb-down the models in order to promote diversity.

The number of component classifiers of an ensemble has a great impact on the accuracy of prediction. A priori determining of ensemble size and the volume and velocity of big data streams make this even more crucial for online ensemble classifiers. A theoretical framework suggests that there are an ideal number of component classifiers for an ensemble such that having more or less than this number of classifiers would deteriorate the accuracy. The theoretical framework shows that using the same number of independent component classifiers as class labels gives the highest accuracy.

Figure 13:
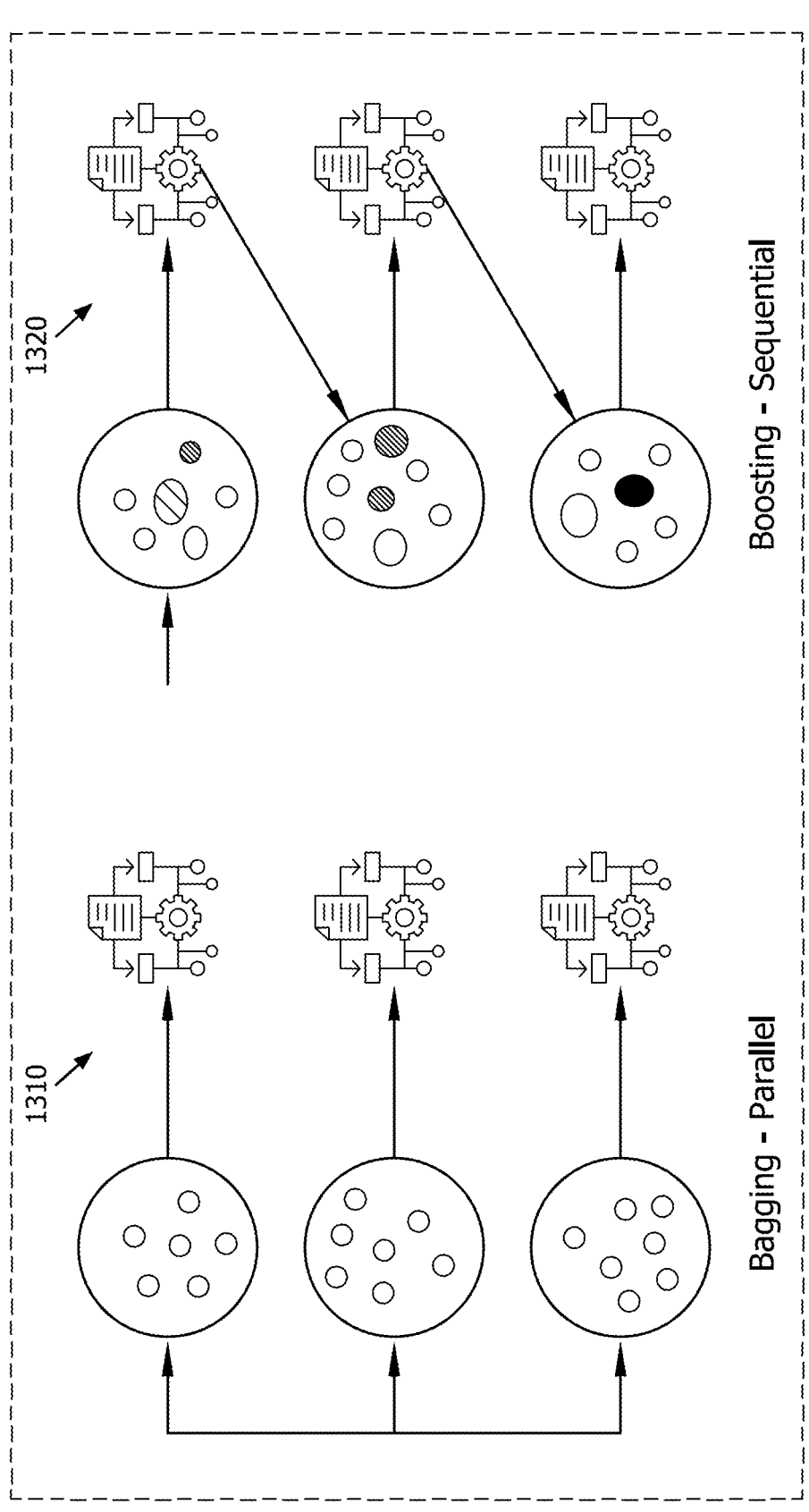
FIG. 13 illustrates an exemplary ensemble learning algorithm.

Some common types of ensembles include Bayes optimal classifier, bootstrap aggregating (bagging), boosting, Bayesian model averaging, Bayesian model combination, bucket of models and stacking. FIG. 13 illustrates an exemplary ensemble learning algorithm where bagging is being performed in parallel 1310 and boosting is being performed sequentially 1320.

A neural network is a network or circuit of neurons, or in a modern sense, an artificial neural network, composed of artificial neurons or nodes. The connections of the biological neuron are modeled as weights. A positive weight reflects an excitatory connection, while negative values mean inhibitory connections. Inputs are modified by a weight and summed using a linear combination. An activation function may control the amplitude of the output. For example, an acceptable range of output is usually between 0 and 1, or it could be −1 and 1.

These artificial networks may be used for predictive modeling, adaptive control and applications and can be trained via a dataset. Self-learning resulting from experience can occur within networks, which can derive conclusions from a complex and seemingly unrelated set of information.

For completeness, a biological neural network is composed of a group or groups of chemically connected or functionally associated neurons. A single neuron may be connected to many other neurons and the total number of neurons and connections in a network may be extensive. Connections, called synapses, are usually formed from axons to dendrites, though dendrodendritic synapses and other connections are possible. Apart from the electrical signaling, there are other forms of signaling that arise from neurotransmitter diffusion.

Artificial intelligence, cognitive modeling, and neural networks are information processing paradigms inspired by the way biological neural systems process data. Artificial intelligence and cognitive modeling try to simulate some properties of biological neural networks. In the artificial intelligence field, artificial neural networks have been applied successfully to speech recognition, image analysis and adaptive control, in order to construct software agents (in computer and video games) or autonomous robots.

A neural network (NN), in the case of artificial neurons called artificial neural network (ANN) or simulated neural network (SNN), is an interconnected group of natural or artificial neurons that uses a mathematical or computational model for information processing based on a connectionistic approach to computation. In most cases an ANN is an adaptive system that changes its structure based on external or internal information that flows through the network. In more practical terms neural networks are non-linear statistical data modeling or decision-making tools. They can be used to model complex relationships between inputs and outputs or to find patterns in data.

An artificial neural network involves a network of simple processing elements (artificial neurons) which can exhibit complex global behavior, determined by the connections between the processing elements and element parameters.

One classical type of artificial neural network is the recurrent Hopfield network. The utility of artificial neural network models lies in the fact that they can be used to infer a function from observations and also to use it. Unsupervised neural networks can also be used to learn representations of the input that capture the salient characteristics of the input distribution, and more recently, deep learning algorithms, which can implicitly learn the distribution function of the observed data. Learning in neural networks is particularly useful in applications where the complexity of the data or task makes the design of such functions by hand impractical.

Neural networks can be used in different fields. The tasks to which artificial neural networks are applied tend to fall within the following broad categories: function approximation, or regression analysis, including time series prediction and modeling, classification, including pattern and sequence recognition, novelty detection and sequential decision making, data processing, including filtering, clustering, blind signal separation and compression.

Application areas of ANNs include nonlinear system identification and control (vehicle control, process control), game-playing and decision making (backgammon, chess, racing), pattern recognition (radar systems, face identification, object recognition), sequence recognition (gesture, speech, handwritten text recognition), medical diagnosis, financial applications, data mining (or knowledge discovery in databases, "KDD"), visualization and e-mail spam filtering. For example, it is possible to create a semantic profile of user's interests emerging from pictures trained for object recognition.

Figure 14:
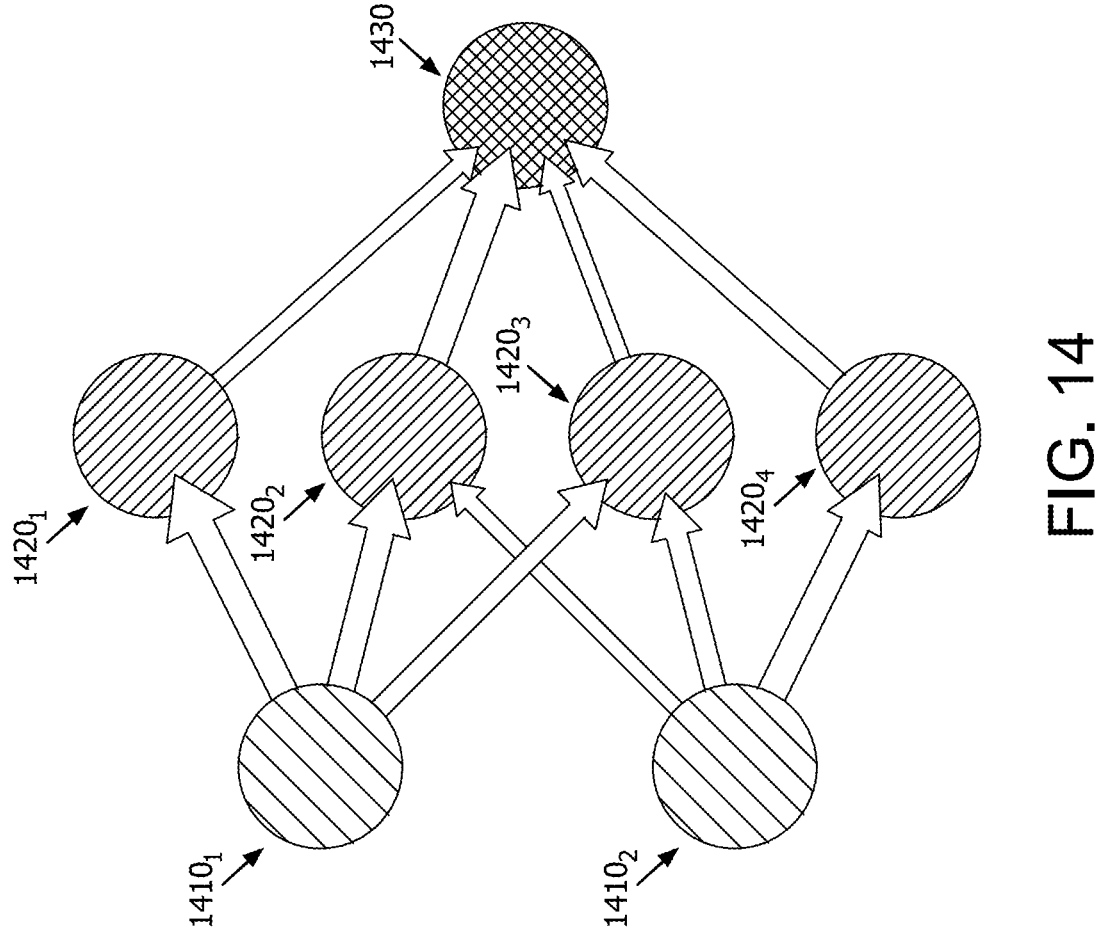
FIG. 14 illustrates an exemplary neural network.

FIG. 14 illustrates an exemplary neural network. In the neural network there is an input layer represented by a plurality of inputs, such as 14101 and 14102. The inputs 14101, 14102 are provided to a hidden layer depicted as including nodes 14201, 14202, 14203, 14204. These nodes 14201, 14202, 14203, 14204 are combined to produce an output 1430 in an output layer. The neural network performs simple processing via the hidden layer of simple processing elements, nodes 14201, 14202, 14203, 14204, which can exhibit complex global behavior, determined by the connections between the processing elements and element parameters.

Figure 15:
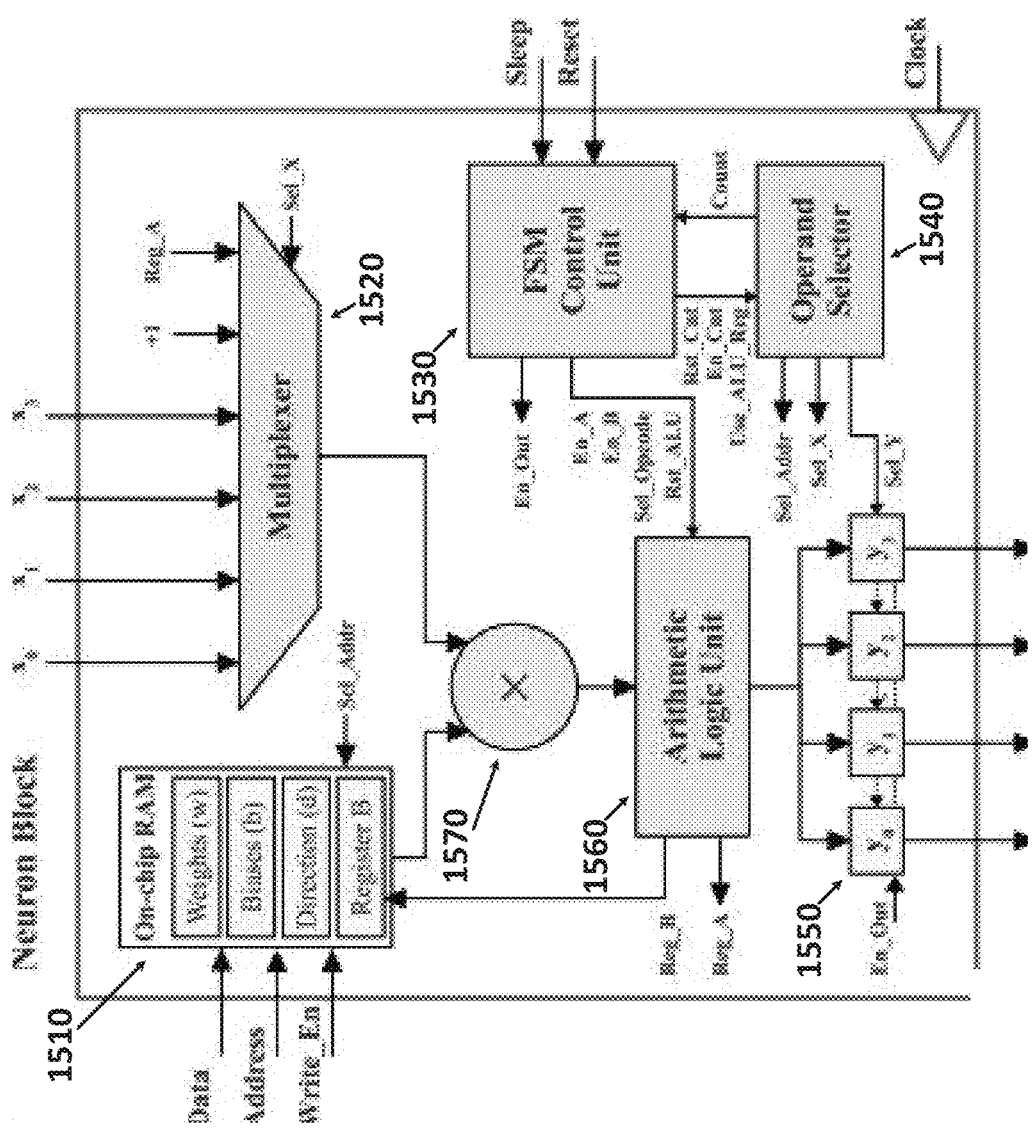
FIG. 15 illustrates a hardware-based neural network.

The neural network of FIG. 14 may be implemented in hardware. As depicted in FIG. 15 a hardware based neural network is depicted.

Treatments for cardiac conditions such as cardiac arrhythmia often require obtaining a detailed mapping of cardiac tissue, chambers, veins, arteries and/or electrical pathways. For example, a prerequisite for performing a catheter ablation successfully is that the cause of the cardiac arrhythmia is accurately located in the heart chamber. Such locating may be done via an electrophysiological investigation during which electrical potentials are detected spatially resolved with a mapping catheter introduced into the heart chamber. This electrophysiological investigation, the so-called electro-anatomical mapping, thus provides 3D mapping data which can be displayed on a monitor. In many cases, the mapping function and a treatment function (e.g., ablation) are provided by a single catheter or group of catheters such that the mapping catheter also operates as a treatment (e.g., ablation) catheter at the same time Mapping of cardiac areas such as cardiac regions, tissue, veins, arteries and/or electrical pathways of the heart may result in identifying problem areas such as scar tissue, arrythmia sources (e.g., electric rotors), healthy areas, and the like. Cardiac areas may be mapped such that a visual rendering of the mapped cardiac areas is provided using a display, as further disclosed herein. Additionally, cardiac mapping may include mapping based on one or more modalities such as, but not limited to local activation time (LAT), an electrical activity, a topology, a bipolar mapping, a dominant frequency, or an impedance. Data corresponding to multiple modalities may be captured using a catheter inserted into a patient's body and may be provided for rendering at the same time or at different times based on corresponding settings and/or preferences of a medical professional.

Cardiac mapping may be implemented using one or more techniques. As an example of a first technique, cardiac mapping may be implemented by sensing an electrical property of heart tissue, for example, local activation time, as a function of the precise location within the heart. The corresponding data may be acquired with one or more catheters that are advanced into the heart using catheters that have electrical and location sensors in their distal tips. As specific examples, location and electrical activity may be initially measured on about 10 to about 20 points on the interior surface of the heart. These data points may be generally sufficient to generate a preliminary reconstruction or map of the cardiac surface to a satisfactory quality. The preliminary map may be combined with data taken at additional points in order to generate a more comprehensive map of the heart's electrical activity. In clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. Maps depicting such motion characteristics may be constructed when the trajectory information is sampled at a sufficient number of points in the heart.

Electrical activity at a point in the heart may be typically measured by advancing a catheter containing an electrical sensor at or near its distal tip to that point in the heart, contacting the tissue with the sensor and acquiring data at that point. One drawback with mapping a cardiac chamber using a catheter containing only a single, distal tip electrode is the long period of time required to accumulate data on a point-by-point basis over the requisite number of points required for a detailed map of the chamber as a whole. Accordingly, multiple-electrode catheters have been developed to simultaneously measure electrical activity at multiple points in the heart chamber.

Figure 16A:
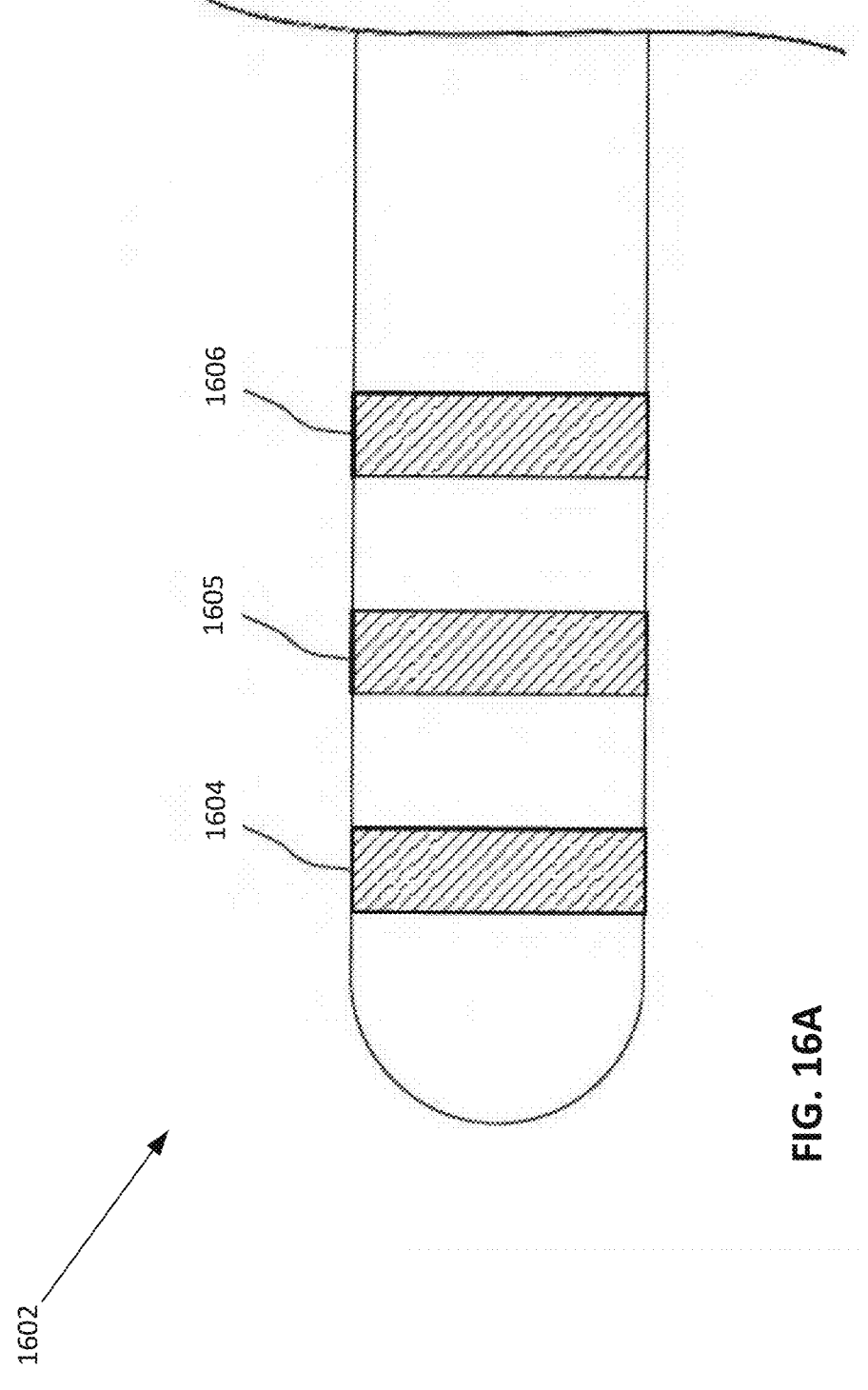
FIGS. 16A through 16C show examples of intra body catheters.

Multiple-electrode catheters may be implemented using any applicable shape such as a linear catheter with multiple electrodes, a balloon catheter including electrodes dispersed on multiple spines that shape the balloon, a lasso or loop catheter with multiple electrodes, or any other applicable shape. FIG. 16A shows an example of a linear catheter 1602 including multiple electrodes 1604, 1605, and 1606 that may be used to map a cardiac area. Linear catheter 1602 may be fully or partially elastic such that it can twist, bend, and or otherwise change its shape based on received signal and/or based on application of an external force (e.g., cardiac tissue) on the linear catheter 1602.

Figure 16B:
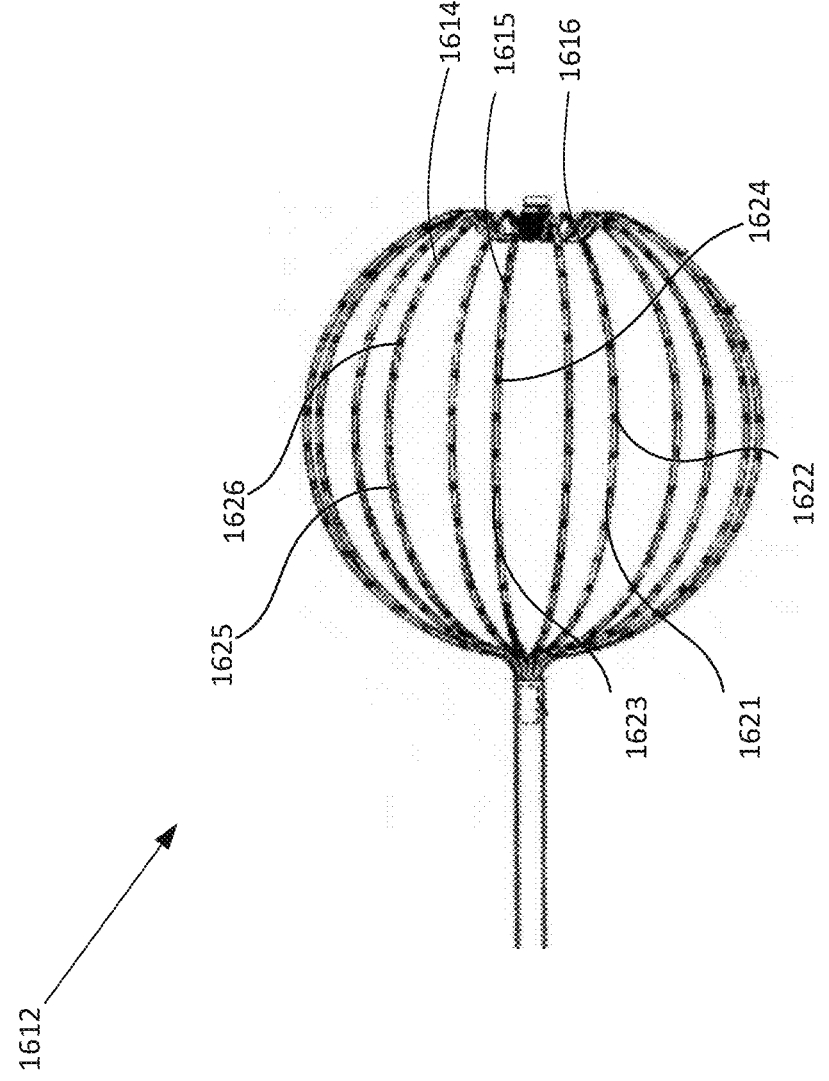

FIG. 16B shows an example of a balloon catheter 1612 including multiple splines (e.g., 12 splines in the specific example of FIG. 16B) including splines 1614, 1616, 1617 and multiple electrodes on each spline including electrodes 1621, 1622, 1623, 1624, 1625, and 1626 as shown. The balloon catheter 1612 may be designed such that when deployed into a patient's body, its electrodes may be held in intimate contact against an endocardial surface. As an example, a balloon catheter may be inserted into a lumen, such as a pulmonary vein (PV). The balloon catheter may be inserted into the PV in a deflated state such that the balloon catheter does not occupy its maximum volume while being inserted into the PV. The balloon catheter may expand while inside the PV such that electrodes on the balloon catheter are in contact with an entire circular section of the PV. Such contact with an entire circular section of the PV, or any other lumen, may enable efficient mapping and/or ablation.

Figure 16C:
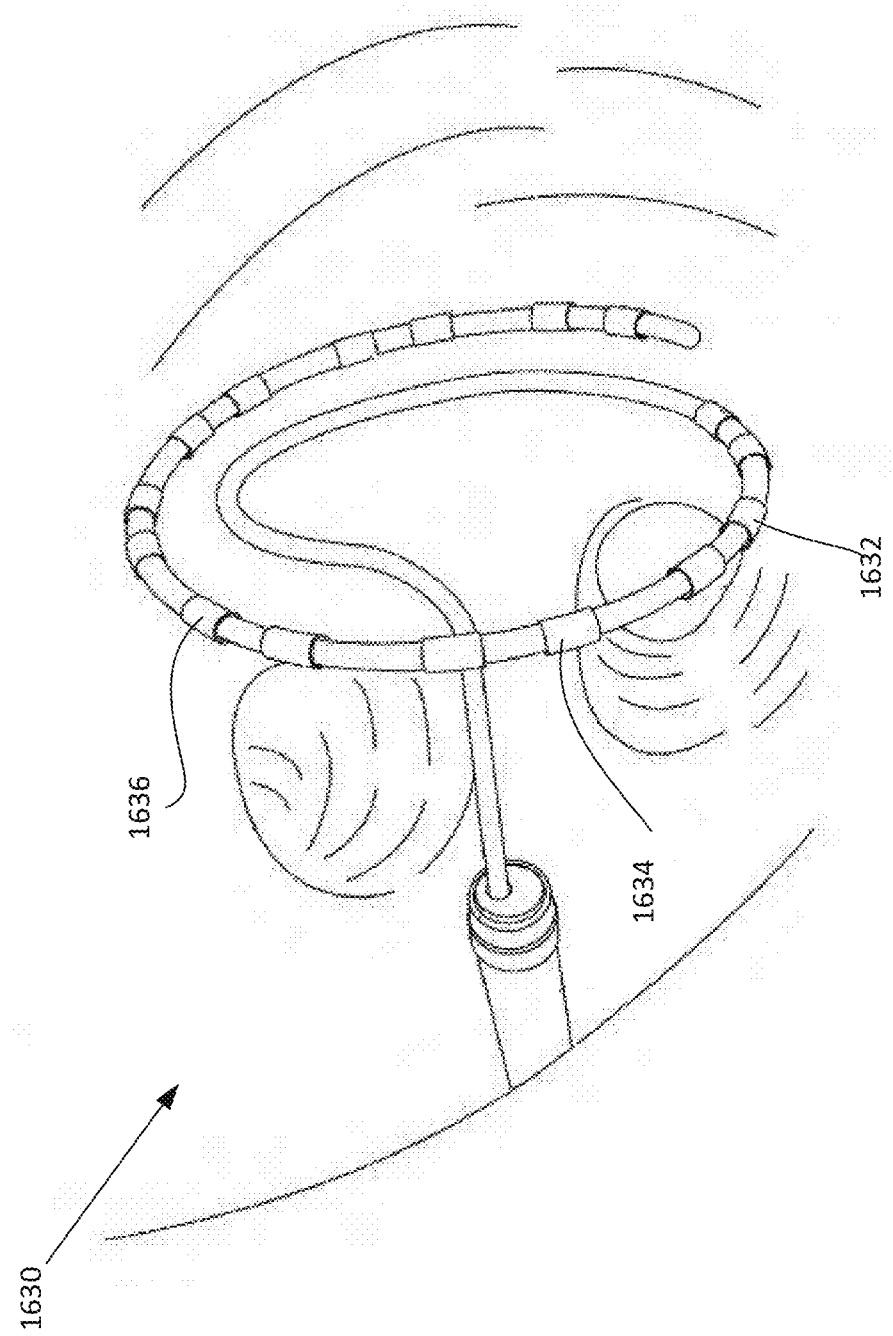

FIG. 16C shows an example of a loop catheter 1630 (also referred to as a lasso catheter) including multiple electrodes 1632, 1634, and 1636 that may be used to map a cardiac area. Loop catheter 1630 may be fully or partially elastic such that it can twist, bend, and or otherwise change its shape based on received signal and/or based on application of an external force (e.g., cardiac tissue) on the loop catheter 1630.

According to an example, a multi-electrode catheter may be advanced into a chamber of the heart. Anteroposterior (AP) and lateral fluorograms may be obtained to establish the position and orientation of each of the electrodes. Electrograms may be recorded from each of the electrodes in contact with a cardiac surface relative to a temporal reference such as the onset of the P-wave in sinus rhythm from a body surface ECG. The system, as further disclosed herein, may differentiate between those electrodes that register electrical activity and those that do not due to absence of close proximity to the endocardial wall. After initial electrograms are recorded, the catheter may be repositioned, and fluorograms and electrograms may be recorded again. An electrical map may then be constructed from iterations of the process above.

According to an example, cardiac mapping may be generated based on detection of intracardiac electrical potential fields. A non-contact technique to simultaneously acquire a large amount of cardiac electrical information may be implemented. For example, a catheter having a distal end portion may be provided with a series of sensor electrodes distributed over its surface and connected to insulated electrical conductors for connection to signal sensing and processing means. The size and shape of the end portion may be such that the electrodes are spaced substantially away from the wall of the cardiac chamber. Intracardiac potential fields may be detected during a single cardiac beat. According to an example, the sensor electrodes may be distributed on a series of circumferences lying in planes spaced from each other. These planes may be perpendicular to the major axis of the end portion of the catheter. At least two additional electrodes may be provided adjacent at the ends of the major axis of the end portion. As a more specific example, the catheter may include four circumferences with eight electrodes spaced equiangularly on each circumference. Accordingly, in this specific implementation, the catheter may include at least 34 electrodes (32 circumferential and 2 end electrodes).

According to another example, an electrophysiological cardiac mapping system and technique based on a non-contact and non-expanded multi-electrode catheter may be implemented. Electrograms may be obtained with catheters having multiple electrodes (e.g., between 42 to 122 electrodes). According to this implementation, knowledge of the relative geometry of the probe and the endocardium may be obtained such as by an independent imaging modality such as transesophogeal echocardiography. After the independent imaging, non-contact electrodes may be used to measure cardiac surface potentials and construct maps therefrom. This technique may include the following steps (after the independent imaging step): (a) measuring electrical potentials with a plurality of electrodes disposed on a probe positioned in the heart; (b) determining the geometric relationship of the probe surface and the endocardial surface; (c) generating a matrix of coefficients representing the geometric relationship of the probe surface and the endocardial surface; and (d) determining endocardial potentials based on the electrode potentials and the matrix of coefficients.

According to another example, a technique and apparatus for mapping the electrical potential distribution of a heart chamber may be implemented. An intra-cardiac multielectrode mapping catheter assembly may be inserted into a patient's heart. The mapping catheter assembly may include a multi-electrode array with an integral reference electrode, or, preferably, a companion reference catheter. The electrodes may be deployed in the form of a substantially spherical array. The electrode array may be spatially referenced to a point on the endocardial surface by the reference electrode or by the reference catheter which is brought into contact with the endocardial surface. The preferred electrode array catheter may carry a number of individual electrode sites (e.g., at least 24). Additionally, this example technique may be implemented with knowledge of the location of each of the electrode sites on the array, as well as a knowledge of the cardiac geometry. These locations are preferably determined by a technique of impedance plethysmography.

According to another example, a heart mapping catheter assembly may include an electrode array defining a number of electrode sites. The mapping catheter assembly may also include a lumen to accept a reference catheter having a distal tip electrode assembly which may be used to probe the heart wall. The mapping catheter may include a braid of insulated wires (e.g., having 24 to 64 wires in the braid), and each of the wires may be used to form electrode sites. The catheter may be readily positionable in a heart to be used to acquire electrical activity information from a first set of non-contact electrode sites and/or a second set of in-contact electrode sites.

According to another example, another catheter for mapping electrophysiological activity within the heart may be implemented. The catheter body may include a distal tip which is adapted for delivery of a stimulating pulse for pacing the heart or an ablative electrode for ablating tissue in contact with the tip. The catheter may further include at least one pair of orthogonal electrodes to generate a difference signal indicative of the local cardiac electrical activity adjacent the orthogonal electrodes.

According to another example, a process for measuring electrophysiologic data in a heart chamber may be implemented. The method may include, in part, positioning a set of active and passive electrodes into the heart, supplying current to the active electrodes, thereby generating an electric field in the heart chamber, and measuring the electric field at the passive electrode sites. The passive electrodes are contained in an array positioned on an inflatable balloon of a balloon catheter. In preferred embodiments, the array is said to have from 60 to 64 electrodes.

According to another example, cardiac mapping may be implemented using one or more ultrasound transducers. The ultrasound transducers may be inserted into a patient's heart and may collect a plurality of ultrasound slices (e.g., two dimensional or three-dimensional slices) at various locations and orientations within the heart. The location and orientation of a given ultrasound transducer may be known and the collected ultrasound slices may be stored such that they can be displayed at a later time. One or more ultrasound slices corresponding to the position of a probe (e.g., a treatment catheter) at the later time may be displayed and the probe may be overlaid onto the one or more ultrasound slices.

According to other examples, body patches and/or body surface electrodes may be positioned on or proximate to a patient's body. A catheter with one or more electrodes may be positioned within the patient's body (e.g., within the patient's heart) and the position of the catheter may be determined by a system based on signals transmitted and received between the one or more electrodes of the catheter and the body patches and/or body surface electrodes. Additionally, the catheter electrodes may sense biometric data (e.g., LAT values) from within the body of the patient (e.g., within the heart). The biometric data may be associated with the determined position of the catheter such that a rendering of the patient's body part (e.g., heart) may be displayed and may show the biometric data overlaid on a shape of the body part, as determined by the position of the catheter.

Figure 17:
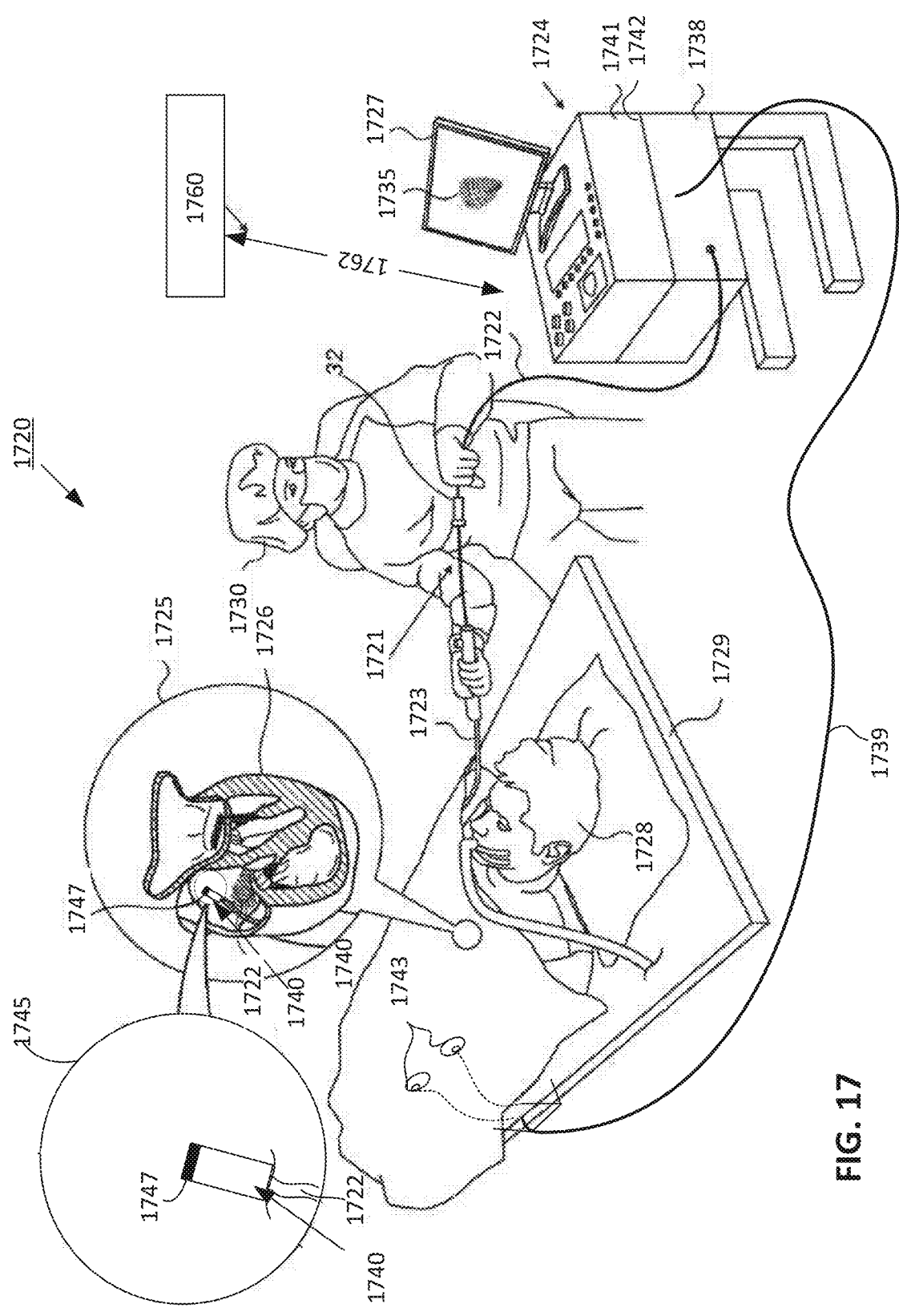
FIG. 17 is a diagram of an exemplary system in which one or more features of the disclosure subject matter can be implemented.

FIG. 17 is a diagram of an exemplary system 1720 in which one or more features of the disclosure subject matter can be implemented. All or parts of system 1720 may be used to collect information for a training dataset and/or all or parts of system 1720 may be used to implement a trained model or trained learning system. System 1720 may include components, such as a catheter 1740, that is configured to obtain biometric data for cardiac mapping and/or configured to damage tissue areas of an intra-body organ. Accordingly, it will be understood that the catheter 1740 may be a mapping catheter, a treatment (e.g., ablation) catheter, or both. The disclosure herein may refer to the catheter 1740 operating as a mapping catheter, a treatment catheter, or both but it will be understood that one or more catheters may be used to implement the subject matter disclosed herein. Although catheter 1740 is shown to be a point catheter, it will be understood that a catheter of any shape that includes one or more elements (e.g., electrodes) may be used to implement the embodiments disclosed herein. System 1720 includes a probe 1721, having shafts that may be navigated by a physician 1730 into a body part, such as heart 1726, of a patient 1728 lying on a table 1729. According to embodiments, multiple probes may be provided, however, for purposes of conciseness, a single probe 1721 is described herein but it will be understood that probe 1721 may represent multiple probes. As shown in FIG. 17, physician 1730 may insert shaft 1722 through a sheath 1723, while manipulating the distal end of the shafts 1722 using a manipulator 1732 near the proximal end of the catheter 1740 and/or deflection from the sheath 1723. As shown in an inset 1725, catheter 1740 may be fitted at the distal end of shafts 1722. Catheter 1740 may be inserted through sheath 1723 in a collapsed state and may be then expanded within heart 1726. Cather 1740 may include at least one ablation electrode 1747 and a catheter needle 1748, as further disclosed herein.

According to embodiments, catheter 1740 may be configured to ablate tissue areas of a cardiac chamber of heart 1726. Inset 1745 shows catheter 1740 in an enlarged view, inside a cardiac chamber of heart 1726. As shown, catheter 1740 may include at least one ablation electrode 1747 coupled onto the body of the catheter. According to other embodiments, multiple elements may be connected via splines that form the shape of the catheter 1740. One or more other elements (not shown) may be provided and may be any elements configured to ablate or to obtain biometric data and may be electrodes, transducers, or one or more other elements.

According to embodiments disclosed herein, the ablation electrodes, such as electrode 1747, may be configured to provide energy to tissue areas of an intra-body organ such as heart 1726. The energy may be thermal energy and may cause damage to the tissue area starting from the surface of the tissue area and extending into the thickness of the tissue area.

According to embodiments disclosed herein, biometric data may include one or more of LATs, electrical activity, topology, bipolar mapping, dominant frequency, impedance, or the like. The local activation time may be a point in time of a threshold activity corresponding to a local activation, calculated based on a normalized initial starting point. Electrical activity may be any applicable electrical signals that may be measured based on one or more thresholds and may be sensed and/or augmented based on signal to noise ratios and/or other filters. A topology may correspond to the physical structure of a body part or a portion of a body part and may correspond to changes in the physical structure relative to different parts of the body part or relative to different body parts. A dominant frequency may be a frequency or a range of frequency that is prevalent at a portion of a body part and may be different in different portions of the same body part. For example, the dominant frequency of a pulmonary vein of a heart may be different than the dominant frequency of the right atrium of the same heart. Impedance may be the resistance measurement at a given area of a body part.

As shown in FIG. 17, the probe 1721, and catheter 1740 may be connected to a console 1724. Console 1724 may include a processor 1741, such as a general-purpose computer, with suitable front end and interface circuits 1738 for transmitting and receiving signals to and from catheter, as well as for controlling the other components of system 1720. In some embodiments, processor 1741 may be further configured to receive biometric data, such as electrical activity, and determine if a given tissue area conducts electricity. According to an embodiment, the processor may be external to the console 1724 and may be located, for example, in the catheter, in an external device, in a mobile device, in a cloud-based device, or may be a standalone processor.

As noted above, processor 1741 may include a general-purpose computer, which may be programmed in software to carry out the functions described herein. The software may be downloaded to the general-purpose computer in electronic form, over a network, for example, or it may, alternatively or additionally, be provided and/or stored on non-transitory tangible media, such as magnetic, optical, or electronic memory. The example configuration shown in FIG. 17 may be modified to implement the embodiments disclosed herein. The disclosed embodiments may similarly be applied using other system components and settings.

Additionally, system 1720 may include additional components, such as elements for sensing electrical activity, wired or wireless connectors, processing and display devices, or the like.

According to an embodiment, a display connected to a processor (e.g., processor 1741) may be located at a remote location such as a separate hospital or in separate healthcare provider networks. Additionally, the system 1720 may be part of a surgical system that is configured to obtain anatomical and electrical measurements of a patient's organ, such as a heart, and performing a cardiac ablation procedure. An example of such a surgical system is the Carto® system sold by Biosense Webster.

The system 1720 may also, and optionally, obtain biometric data such as anatomical measurements of the patient's heart using ultrasound, computed tomography (CT), magnetic resonance imaging (MRI) or other medical imaging techniques known in the art. The system 1720 may obtain electrical measurements using catheters, electrocardiograms (EKGs) or other sensors that measure electrical properties of the heart. The biometric data including anatomical and electrical measurements may then be stored in a memory 1742 of the mapping system 1720, as shown in FIG. 17. The biometric data may be transmitted to the processor 1741 from the memory 1742. Alternatively, or in addition, the biometric data may be transmitted to a server 1760, which may be local or remote, using a network 1762.

Network 1762 may be any network or system generally known in the art such as an intranet, a local area network (LAN), a wide area network (WAN), a metropolitan area network (MAN), a direct connection or series of connections, a cellular telephone network, or any other network or medium capable of facilitating communication between the mapping system 1720 and the server 1760. The network 1762 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 1762.

In some instances, the server 1762 may be implemented as a physical server. In other instances, server 1762 may be implemented as a virtual server a public cloud computing provider (e.g., Amazon Web Services (AWS)®).

Control console 1724 may be connected, by a cable 1739, to body surface electrodes 1743, which may include adhesive skin patches that are affixed to the patient 1730. The processor, in conjunction with a current tracking module, may determine position coordinates of the catheter 1740 inside the body part (e.g., heart 1726) of a patient. The position coordinates may be based on impedances or electromagnetic fields measured between the body surface electrodes 1743 and the electrode 1748 or other electromagnetic components of the catheter 1740. Additionally, or alternatively, location pads may be located on the surface of bed 1729 and may be separate from the bed 1729.

Processor 1741 may include real-time noise reduction circuitry typically configured as a field programmable gate array (FPGA), followed by an analog-to-digital (A/D) ECG (electrocardiograph) or EMG (electromyogram) signal conversion integrated circuit. The processor 1741 may pass the signal from an A/D ECG or EMG circuit to another processor and/or can be programmed to perform one or more functions disclosed herein.

Control console 1724 may also include an input/output (I/O) communications interface that enables the control console to transfer signals from, and/or transfer signals to electrode 1747.

During a procedure, processor 1741 may facilitate the presentation of a body part rendering 1735 to physician 1730 on a display 1727, and store data representing the body part rendering 1735 in a memory 1742. Memory 1742 may comprise any suitable volatile and/or non-volatile memory, such as random-access memory or a hard disk drive. In some embodiments, medical professional 1730 may be able to manipulate a body part rendering 1735 using one or more input devices such as a touch pad, a mouse, a keyboard, a gesture recognition apparatus, or the like. For example, an input device may be used to change the position of catheter 1740 such that rendering 1735 is updated. In alternative embodiments, display 1727 may include a touchscreen that can be configured to accept inputs from medical professional 1730, in addition to presenting a body part rendering 1735.

According to exemplary embodiments of the disclosed subject matter, new CPM matrices may be generated based on historical CPM matrices, with little or no corresponding catheter location information. Notably, the techniques disclosed herein may enable the generation of CPM matrices without using an intrabody catheter to physically cover an entire cardiac chamber to determine ratios for each location. Advantageously, new, supplemented CPM matrices may be generated based on sparse, CPM matrices, so the time required to generate a CPM matrix with increased resolution is drastically reduced (as such a process would typically require moving an intrabody catheter to locations in the heart and collecting location data and data associated with patient properties—e.g., electrical signals of the heart).

In a supplemented CPM matrix, a density of the mapping between the patient properties (e.g. electrical signals) and location will be higher than that of the sparse CPM matrix. In one example, an electrical signal with a corresponding location will be collected in each 3 mm$^3$ voxel of a heart, to generate a sparse CPM matrix. However, an electrical signal with a corresponding location can be collected in more locations (e.g. in each 1 mm$^3$ voxel) of a heart, to generate a supplemented CPM matrix. As noted above, a new, supplemented matrix having said higher density of mapping can be generated solely on a calculated sparse CPM matrix provided to a learning system.

A historical CPM matrix may be generated for each given catheter location (e.g., based on a corresponding cluster) based on the current distribution from a signal transmitted from an intrabody catheter electrode and received by a plurality of body surface (BS) patches on the patient's body.

Figure 18A:
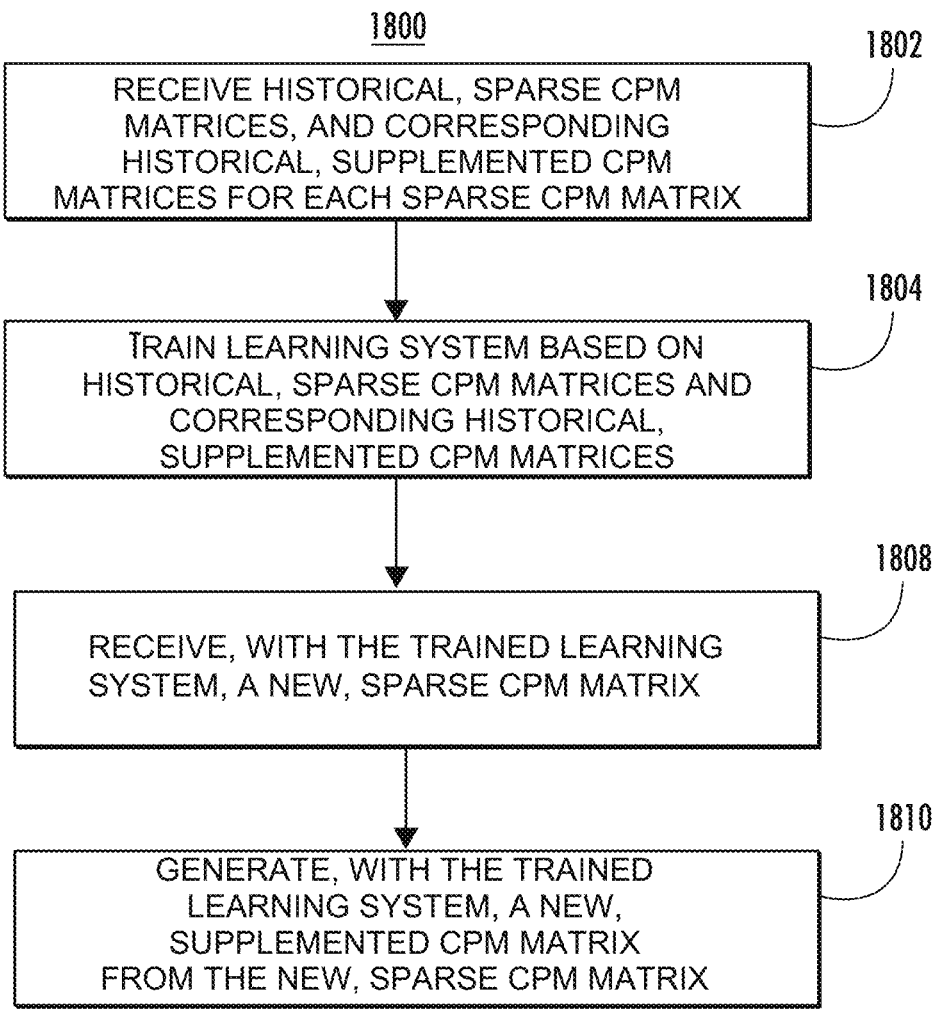
FIG. 18a is a flowchart for generating supplemented current to position mappings (CPMs) from sparse CPMs for multiple locations.

FIG. 18a shows a process 1800 according to an embodiment of the invention for determining a new, supplemented CPM matrix from a sparse, CPM matrix. FIG. 18b shows an alternative or additional process 1800 for determining catheter locations based on new electrical signals and generating CPM matrices without new catheter location information corresponding to the new electrical signals. To clarify, numerous instances of historical CPM matrices with corresponding patient properties (e.g., electrical signals, catheter orientation and/or position, heart anatomy, etc.) and catheter locations may be used as training data to generate a model in accordance with FIGS. 4-15, as provided herein. For the avoidance of doubt, it is be understood that a "generated model" can refer to the same feature as a "trained learning system". In other words, a "generated model" or a "trained learning system" can both refer to a feature that is trained so as to receive an input (e.g. a sparse CPM matrix) and to generate an output given said input (e.g. generate a supplemented CPM matrix given the sparse CPM matrix). The model/learning system is configured to be "trained" on the basis of the training data, so that the model/learning system can determine a relationship between inputs and outputs of the training data. Based on the trained components of the model/learning system, an improved, supplemented CPM matrix may be identified, which can then be used to predict catheter location given a received electrical signal. This implementation would expedite the generation of CPM matrices as it would reduce the need for capturing location information and corresponding ratios for each catheter position.

According to some examples, there is provided a second model that may be trained such that a new electrical signal transmitted by electrodes of a catheter may be captured by, for example, BS patches, and may be fed into the model along with patient properties. Alternatively, or in addition, the second model may be trained such that new electrical signals are transmitted by BS patches and received by electrodes of a catheter, and may be fed into the model along with patient properties. Based on the trained components of the second model, a catheter location may be predicted and CPM matrices may be identified. This implementation would expedite the generation of CPM matrices as it would reduce the need for capturing location information and corresponding ratios for each catheter position.

As shown in flowchart 1800 of FIG. 18a, at step 1802, historical, sparse CPM matrices and historical, supplemented CPM matrices may be collected. At step 1804 of process 1800 of FIG. 18a, the historical, sparse CPM the corresponding, historical, supplemented CPM collected at step 1802 may be used as training data for a learning system. At step 1804, the training data may be used to train the learning system based on a given algorithm. The learning system may be trained such that given a new, sparse CPM matrix, the trained learning system is configured to provide new, supplemented CPM matrices as outputs with minimal catheter locations or with no catheter locations.

At step 1808 of the process 1800 of FIG. 18a, new patient properties (e.g., electrical signals, catheter orientation and/or position, heart anatomy, etc.) for a patient may be received by or provided as input to the model generated at step 1806. At step 1810, the model may output predicted catheter locations and/or generate new CPM matrices based on the input electrical signals.

As shown in flowchart 1800 of FIG. 18b, at step 1802, historical CPM matrices, certain patient properties (e.g., electrical signals, catheter orientation and/or position, heart anatomy, etc.), and corresponding catheter locations may be collected. The corresponding catheter locations may be catheter locations that are identified (e.g., via magnetic mapping electrode) when electrical signals for the corresponding CPM matrix is generated. At step 1804 of process 1800 of FIG. 18, the historical CPM, patient properties, and corresponding locations collected at step 1802 may be used as training data for a learning system. At step 1804, the training data may be used to train the learning system based on a given algorithm. At step 1806 of the process of 1800, the trained learning system may be used to generate a model. The model may be generated such that given new patient properties (e.g., electrical signals, catheter orientation and/or position, heart anatomy, etc.), the model is configured to provide new CPM matrices as outputs with minimal catheter locations or with no catheter locations.

Figure 19:
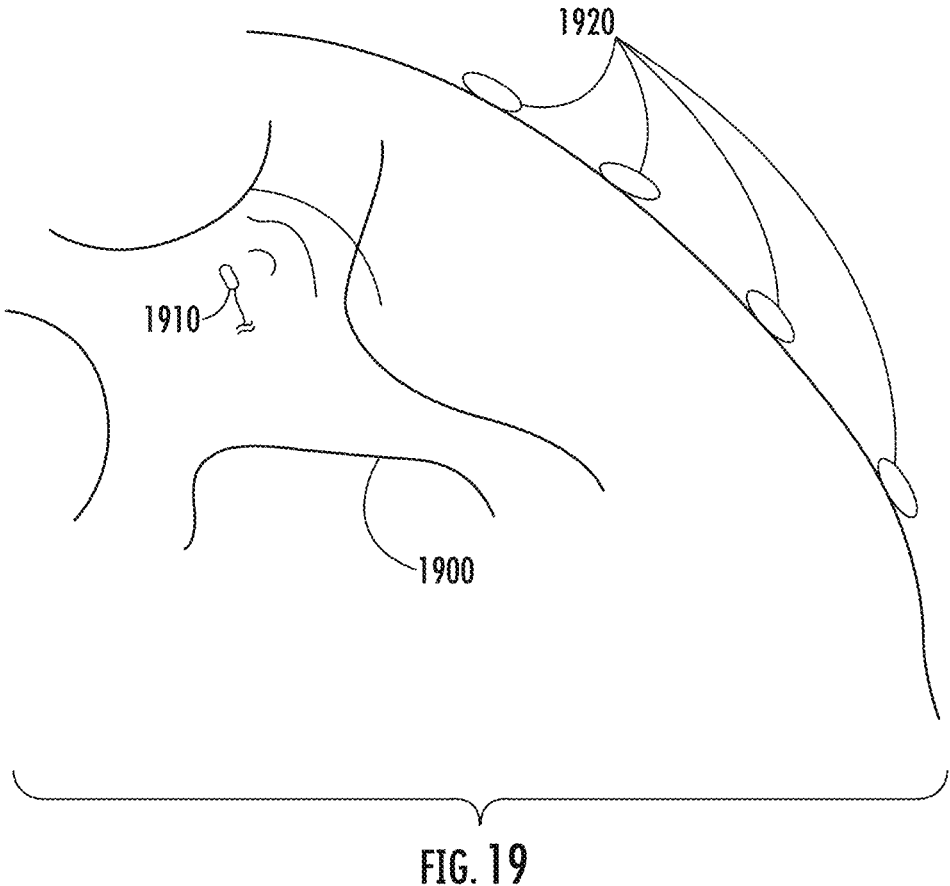
FIG. 19 shows example generation of CPMs using body surface patches.

At step 1808 of the process 1800 of FIG. 18*b*, new patient properties (e.g., electrical signals, catheter orientation and/or position, heart anatomy, etc.) for a patient may be received by or provided as input to the model generated at step 1806. At step 1810, the model may output predicted catheter locations and/or generate new CPM matrices based on the input electrical signals. FIG. 19 shows an example implementation for collecting electrical signals. As shown, a catheter 1910 may be inserted in a cardiac chamber (e.g., a cluster) 1900 and may comprise an electrode configured to emit electrical signals. The electrical signals may be received by one or more BS patches 1920 such that CPM matrices can be generated based on the received electrical signals emitted by the catheter 1910. According to an alternative implementation, as shown in FIG. 19, a catheter 1910 may be inserted in a cardiac chamber (e.g., a cluster) 1900 and may comprise an electrode configured to receive electrical signals. The electrical signals may be transmitted by one or more BS patches 1920 such that CPM matrices can be generated based on the received electrical signals at catheter 1910, as transmitted by the BS patches 1920.

As shown in flowchart 1800 of FIG. 18*a* or FIG. 18*b*, at step 1802, historical CPM matrices and corresponding catheter locations may be received. The historical CPM matrices may be generated based on an adaptive CPM estimation process and a CPM application process. CPM application process may further comprise a cluster selection module, and a CPM application module.

The adaptive CPM estimation process uses measurements from any hybrid catheter having an EM sensor and associated electrode, such as a catheter, the measurements being included in vectors $\vec{m}$, to calculate CPM matrices. In exemplary embodiments of the present invention, a respective matrix is calculated for each sub-volume, also herein termed a cluster volume or a cluster, of the region being investigated. The region being investigated is divided into different sizes of clusters according to a resolution set for a particular cluster level. Thus, at a low-resolution level the region may be divided into, for example, sixteen clusters, each cluster having a matrix. At a higher resolution, the region may be divided into, for example, one thousand and twenty-four, clusters having respective matrices.

The matrices constructed in the historical CPM estimation process take time to build, so that there is an initialization period for an active current location (ACL) step during which period a processor receives initial data from a decomposition step. For a particular cluster, once the processor has accumulated sufficient data for that cluster, the processor is able to generate a matrix for the cluster.

The historical CPM application uses the generated matrices, with current measurements for cathode electrodes, to calculate each electrode location in real-time. The calculation is performed according to the following equation:

$$\vec{p} = A \cdot \vec{m}$$

where $\vec{m}$, is the CPM vector built from the temporally decomposed current measurements, A is the matrix for a particular cluster, and $\vec{p}$, is the position vector of the electrode.

The CPM vector $\vec{m}$, typically has the following four sets of elements: (i) multiple (e.g., five) current elements, corresponding to the values for a mapping catheter, and (ii) multiple (e.g., six) patch respiration indicators $\vec{Rsi}$, corresponding to the Rli values. In addition to the above elements, if a reference catheter such as is used, vector $\vec{m}$, may also comprise: (iii) multiple (e.g., five) reference catheter current elements, and (iv) multiple (e.g., three) reference catheter location elements. The elements in sets (ii), (iii), and (iv) may be values derived after the temporal decomposition described above, i.e. minus the drift component for set (ii), and minus the respiration component in sets (iii) and (iv).

A processor may use the respiration indicators $\vec{Rsi}$, to generate a respiration descriptor, which is a value indicating at which time a measurement is in the respiration cycle. The respiration descriptor is typically generated initially, once a patient is positioned and after patches i have been attached. During a respiration training period, typically of the order of approximately thirty seconds, a processor accumulates values of the respiration indicators $\vec{Rsi}$.

Once respiration indicators have been accumulated, the processor performs principal component analysis (PCA) on the indicators to find a direction between the elements having a largest eigenvalue as follows:

$$\vec{Rdir} = EigenVector\left[\vec{Rs_i} - Mean\left(\vec{Rs_i}\right)\right] \cdot \left[\vec{Rs_i} - Mean\left(\vec{Rs_i}\right)\right]^T \Big|_{\substack{Max \\ (eigen-value)}}$$

The direction given by the equation above is used to calculate a respiration descriptor value as follows:

$$RD_i = \vec{Rdir} \cdot \vec{Rs_i}$$

where RDi is the respiration descriptor for the $i^{th}$ patch.

The mean and range of the RDi values are calculated as follows:

$$RDmean = \frac{1}{N}\sum_{i=1}^{n} RD_1; \vec{RDrange} = Max(RD_i) - Min(RD_i)$$

The mean and range are used to calculate a normalized value RDni of RDi that is in a range from 0 to a maximum value CINo. CLNo is a number defining a resolution of an update holder, described below, and is typically approximately 5.

$$RDn_i = \frac{RD_i - Rmean + \frac{Rrange}{2}}{\vec{Rrange}} CiNo$$

The values of RDni are stored in a memory.

Figure 20:
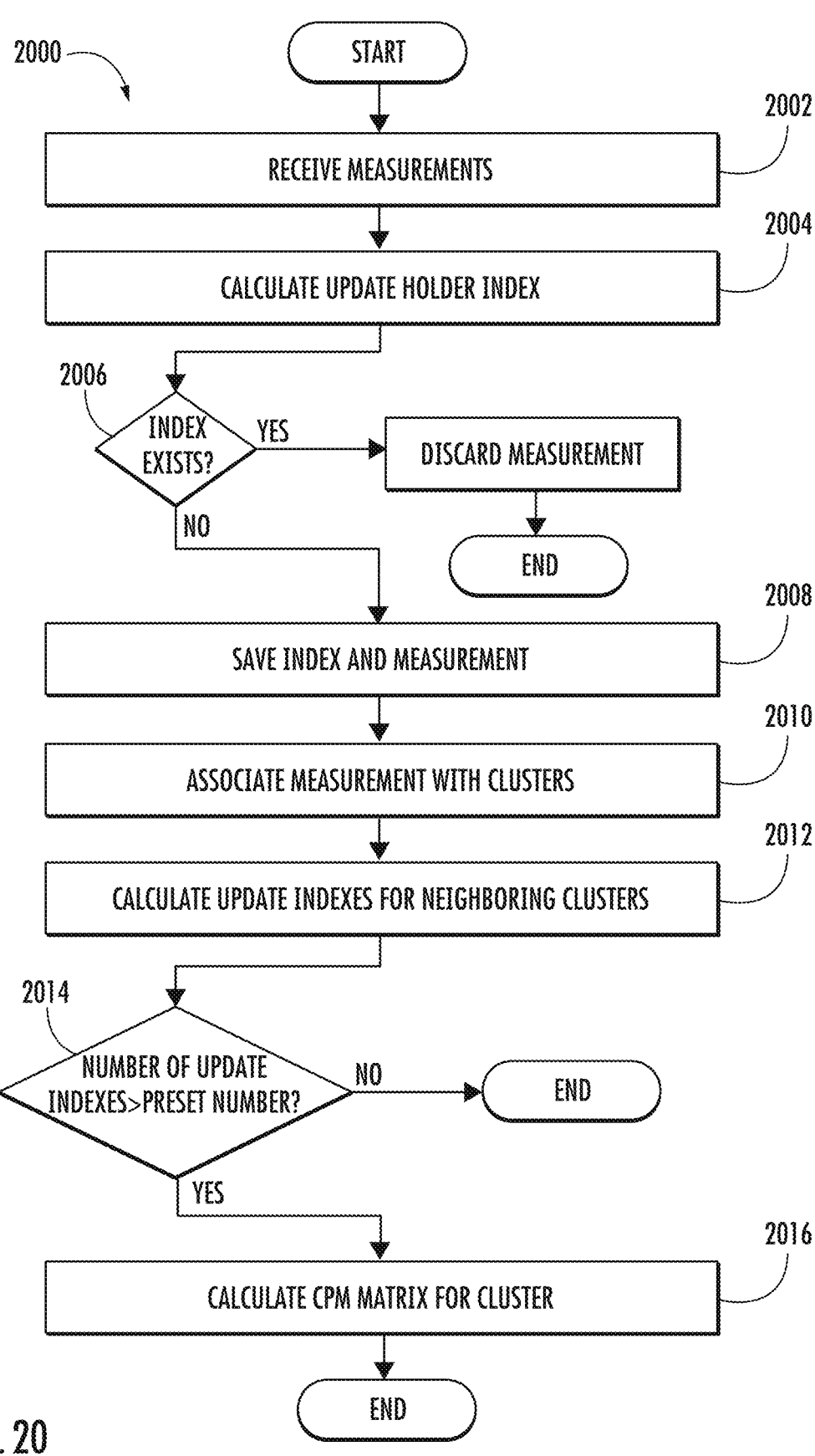
FIG. 20 shows a flowchart for determining historical CPMs.

FIG. 20 is a process 2000 showing steps taken by a processor to generate CPM matrices, according to an embodiment of the present invention. The steps of the process 2000 are performed in adaptive CPM estimation process as each measurement is generated by a catheter.

In an initial step 2002, measurements are received from any hybrid catheter, and the processor forms the measurements into a CPM vector $\vec{m}$, as described herein.

In a first update holder step 2004, the update holder index for the measurement is calculated. In a first condition 2006, the processor checks to see if the update holder index already exists, by checking to see if the index has been saved in memory. If the index does exist, the measurement is discarded and the process ends.

If the index does not exist, then in a save step 2008 the index and the measurements may be saved in a memory buffer. The measurements are saved as a vector $\vec{m}$.

In a cluster association step 2010, the measurement is associated with corresponding clusters. The association is performed by calculating from the measurement the corresponding cluster index. The measurement is associated with this cluster index.

The cluster origin, $\vec{C}lp_{RL}$, is then calculated. From this point, the cluster origins of all existing nearest neighbor clusters, up to 26 of which are possible in total, are found. From the values of $\vec{C}lp_{RL}$, the cluster indexes of all the nearest neighbor clusters are calculated from equation. The calculations in this step are applied for all values of RL.

In a second update holder step 2012, the update holder indexes for the neighboring clusters are calculated using the measurement received in step 2002. If an update index is not already occupied, the measurement is placed in a buffer, and the index is saved. If the index is already occupied, no action is taken.

In a second condition 2014, the number M of update indexes in each cluster Clx is evaluated. If M is larger than a preset number, typically of the order of 40, then in a cluster matrix step 2016 the CPM matrix A of the cluster is calculated, using equation:

$$A_{Clx,RL}=[\vec{m}_1,\cdot\vec{m}_2,\cdot\ldots\ \vec{m}_M]^{-1}\cdot[\vec{p}_1,\cdot\vec{p}_2\cdot\ldots\ \vec{p}_M]$$

where $\vec{p}_n$ is the measured location of the hybrid catheter, and $\vec{m}_n$ is the CPM vector, described herein for update index n, n=1, 2, . . . M.

Two CPM matrices A may be calculated for each cluster, one using measurements with a reference catheter and one without the reference catheter measurements, and process 2000 then ends.

If in condition 2014 M is not larger than the preset number, process 2000 ends.

The calculations in process 2000 are checked at various stages, to verify that the calculated results are self-consistent. For example, in cluster association step 2010, if the number of existing neighboring clusters is less than a preset number, for example four, an error may be assumed and the measurement of step 2002 is not accepted. Other self-consistency checks for the operation of the process will be apparent to those having ordinary skill in the art.

Accordingly, historical CPM matrices based on corresponding catheter locations may be generated in accordance with process 2000 of FIG. 20. At step 1802 of process 1800 of FIG. 18*a* and FIG. 18*b*, the historical CPM matrices may be received along with corresponding patient properties (e.g., electrical signals, catheter orientation and/or position, heart anatomy, etc.) for each given historical CPM matrix. As further disclosed herein, historical CPM matrices may be provided for a large plurality of patients. The large plurality of patients may be, for example, over 100 patients, over 1000 patients, over 10,000 patients, or the like. The number of patients whose historical CPM data is used may depend on one or more of the qualities of the CPM data and corresponding catheter location, which may be determined on a case by case basis.

According to an implementation, the CPM matrices provided for the large plurality of patients may correspond to procedures where accurate matrices were generated based on the patient properties (e.g., electrical signals, catheter orientation and/or position, heart anatomy, etc.) and corresponding catheter locations. For example, a set of one hundred patients' sets of CPM data may be available to train a system, as further disclosed herein. From the one hundred available sets of CPM data, only 70 sets may correspond to procedures where a quality threshold is met. The 70 sets may be used as training data for the embodiments disclose herein. In contrast, the 30 sets that do not meet the quality threshold may not be included as training data.

At step 1804 of the process 1800 of FIG. 18*a*, the historical, sparse CPM matrices and corresponding supplemented CPM matrices may be used to train a learning system. The training may be conducted using hardware, software, and/or firmware. The training may include an analysis and correlation of the CPM matrices and corresponding supplemented CPM matrices received at step 1802. Notably the learning system is configured to determine if a correlation or link exists between each of the sparse CPM matrices and the respective supplemented CPM matrixes.

At step 1804 of the process 1800 of FIG. 18*b*, the historical CPM matrices and corresponding catheter locations may be used to train a learning system. The training may be conducted using hardware, software, and/or firmware. The training may include an analysis and correlation of the CPM matrices, patient properties (e.g., electrical signals, catheter orientation and/or position, heart anatomy, etc.), and corresponding catheter locations received at step 1802. Notably the CPM matrix values at given catheter locations may be used to determine if a correlation or link exists between a given value or set of values and the corresponding catheter location (e.g., if a given set of matrix value correlates to a given catheter location).

Features of the CPM matrices, patient properties, and catheter locations collected at step 1802 may be extracted and may include patterns, relationships, correlations, electrical signals, catheter orientation and/or position, heart anatomy, and the like. A feature matrix may be generated based on the extracted features and the learning system may be trained at step 1804. According to an implementation, the learning system may be trained based on a machine learning algorithm.

The learning system may be trained using an algorithm (to provide a trained learning system and/or generate a model at step 1806). The algorithm may be, for example, a classification algorithm, a regression algorithm, a clustering algorithm, or any applicable algorithm that is able to use the ECG data to generate a model that predicts arrhythmia locations.

Figure 21:
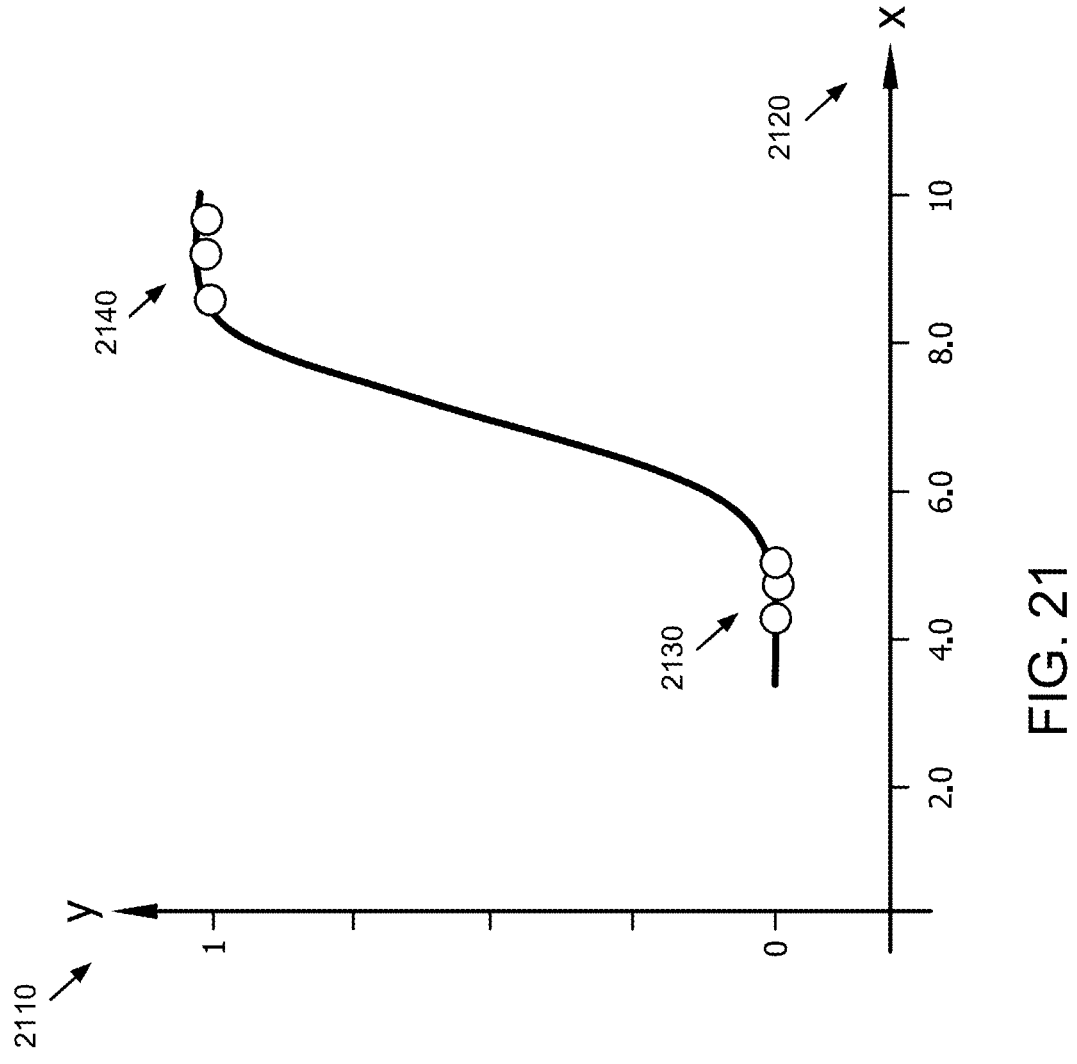
FIG. 21 is an example logistic regression diagram to predict CPMs and cardiac locations.

As an example, FIG. 21 shows a logistic regression diagram to predict whether certain patient properties (e.g., electrical signals, catheter orientation and/or position, heart anatomy, etc.) are likely to correspond to a given catheter location within a heart. This logistic regression subsequently enables the prediction of a cardiac location and corresponding CPM matrix ratios based on the patient properties input into the model. For example, based on plurality patient properties such as a given heart anatomy and electrical signals emitted at first time, an outcome of corresponding cardiac location may be provided by the logistic regression model. The past history of the combination of given patient properties and the relationship with a specific cardiac location enables the prediction to occur. The logistic regression of FIG. 21 enables the analysis of the combination of given patient properties (e.g., heart anatomy and received electrical signals) represented by variables 2120 to map to a given cardiac location, for example, a cluster in the left atrium, where probability 2110 is defined by 0 to 1. At the low end 2130 of the S-shaped curve, a combination of given patient properties 2120 may correspond to an outcome 2110 of not being in the left atrium. While at the high end 2140 of the S-shaped curve, the combination 2120 predicts an outcome 2110 of being in the left atrium.

As stated, a large number of various combinations of such features (e.g., patient properties) may be used to generate a plurality of logistic regression-based outcomes, each predicting a likelihood of cardiac location and respective CPM matrices. The combination of all such logistic regression-based outcomes may be used to generate a logistic regression model at step 1906 that is generated based on the training of the learning system at step 1904.

It will be understood that although a logistic regression-based model is provided as an example, any applicable algorithm (e.g., classification, regression clustering, etc.) may be used to generate a respective model at step 1906.

Once ample training data (e.g., features) are used to train the learning system and generate an applicable model and/or a trained learning system, the model/trained learning system may be used with new data. At step 1908, a new patient property (e.g., electrical signals, catheter orientation and/or position, heart anatomy, etc.) may be applied to the model trained learning system and the model trained learning system may extract features from the new patient properties. A feature vector may be generated and input into the model generated at 1906. The model may use the feature vector as inputs (e.g., as shown in FIG. 15) and may predict supplemented CPM matrices from sparse, CPM matrices. Alternative models/trained learning systems may use the feature vector as inputs and may predict CPM matrices and/or cardiac locations based on the patient properties. According to this alternative, a subset of generated CPM matrices and corresponding known cardiac locations may be provided to the model/trained learning system such that the model/trained learning system outputs the remainder of the CPM matrices corresponding to unknown cardiac locations.

A system and method for producing location estimations for each electrode of a catheter, based on measurements of electrical current by chest patches are disclosed. The system and method estimate the location of a catheter's electrode given measurements of electrical current recorded by the patches (6, for example) which are placed on the patient's chest. A catheter contains electrodes (22, for example, with 2 on the main stem, and 4 on each of the 5 arms as illustrated in FIG. 16B). Each electrode on the catheter emits electrical current in a different frequency. The current travels through the body, until it reaches the sensors on the patches, and the sensors produce readings of the current. When the electrode is located at a certain position, the patches produce one or more vector measurements describing electrical current distribution and respiration indicators. This vector may be referred to as VEC. The system and method may produce an estimation of the electrode's location (in the 3D space), given VEC.

One method for estimating the electrode's location utilizes the Electromagnetic (EM) sensor located on the catheter's main stem. The position of the EM sensor in the 3D space may be known with. One of the electrodes on the catheter referred to as the mapping electrode is the electrode which is placed right next to the EM sensor at a given distance on the inflexible catheter stem, and therefore its position in the 3D space may be known with accuracy given the position based on the EM sensor.

When the physician moves the catheter around the heart, the system collects at each point the measurements of the mapping electrode's known position (based on the EM sensor) together with VEC for the mapping electrode. The system and method may construct a Current to Position Mapping (CPM): The CPM includes a mapping from a VEC value to the voxel where the mapping electrode visited and led to the VEC values at that position.

The CPM may include estimations for other nearby voxels where the mapping electrode has not yet visited. The estimation at a certain voxel is currently produced by linear interpolation of VEC values from nearby voxels for which both VEC and position values are known with certainty.

The system and method may utilize the CPM to estimate the 3D position of an electrode. That is, given a VEC value for an electrode, the CPM is utilized to locate which voxel contains this VEC value. This voxel indicates the 3D position of the electrode.

Initially, as the CPM is very small, not all VEC values of an electrode can be found in the CPM, and thus no location for the electrode can be estimated. As the catheter visits more distinct positions in the heart, the CPM may become more comprehensive, and location estimations for electrodes become available for more locations. The location estimations may become more accurate as more measurements are collected.

Figure 22:
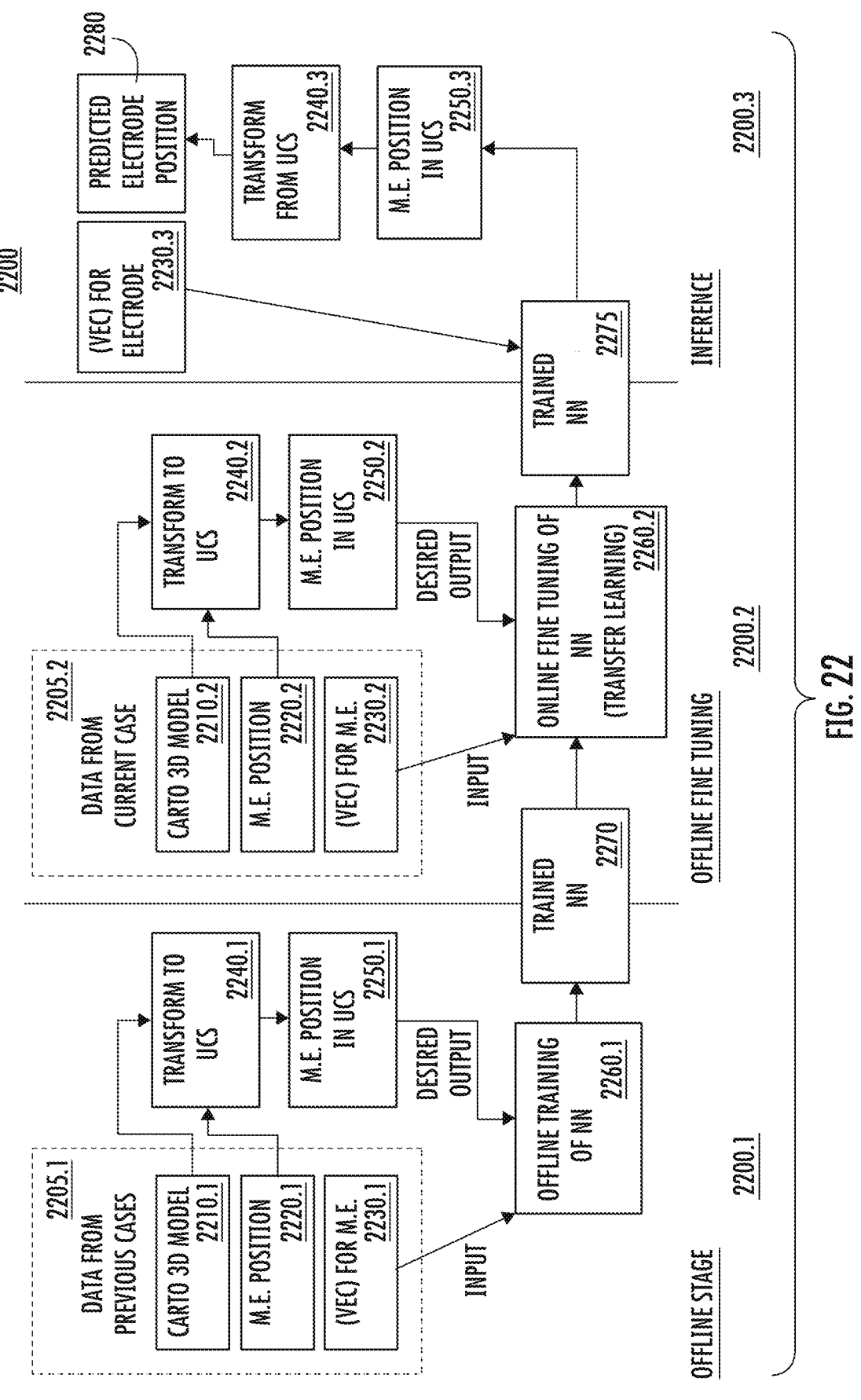
FIG. 22 illustrates a system configuration for predicting the electrode position.

FIG. 22 illustrates a system 2200 configuration for predicting the electrode position. In FIG. 22 "M.E." or "ME" denotes the Mapping Electrode. System 2200 includes a neural network (NN) 2260 which can output an estimation of an electrode's position 2280 given the VEC values 2230.3 for this electrode. The NN 2260 can be trained "on the fly" 2200.3 for a new patient 2275 by using the measurements from the EM sensor and the ME 2250.3, and then applied on VEC measurements 2230.3 for other electrodes to estimate their locations. On a given patient, the NN is not trained from "tabula rasa," because there are not enough measurements in a given patient's data. Instead, the NN 2260vis initialized offline 2200.1 by training the NN 2260.1 on data collected from previous patients 2205.1, as well as on data collected from a simulated model. Then, on a new patient, Transfer Learning 2260.2 is utilized to update the NN model 2260 based on measurements from the specific patient 2205.2. Because the structures of different hearts vary, training of the NN 2260 cannot be done on the raw measurements collected from previous patients 2205.1. Registration (alignment) is required, i.e. transforming the raw data into a universal coordinate system 2240.1.

Figure 23:
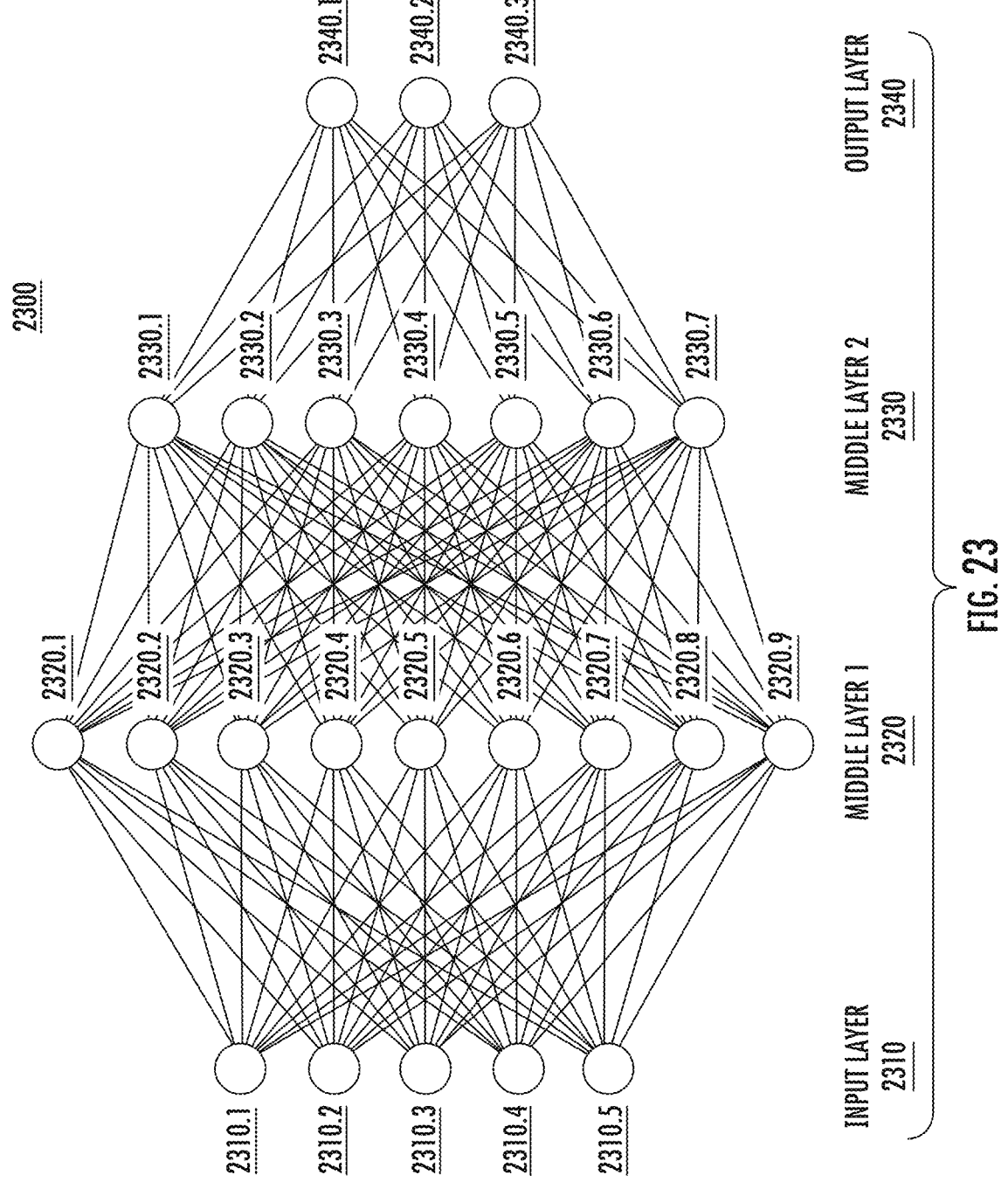
FIG. 23 illustrates a configuration of the NN that may function as NN.

Referring now also to FIG. 23 illustrating a configuration of the core of the NN 2300 that may function as NN 2260. FIG. 23 is described with reference also to FIG. 14. The NN 2300 functioning as NN 2260 may include several layers. The input layer 2310 (represented as five nodes 2310.1, 2310.2, 2310.3, 2310.4, 2310.5) includes a vector representing a VEC measurement. The output layer 2340 (represented as 3 nodes 2340.1, 2340.2, 2340.3) includes a vector of 3 values representing a position in the 3D space. The number and size of the middle layers 2320, 2330, and their architecture may be varied. As illustrated in FIG. 23, there is a middle layer 1 2320 (represented as 9 nodes 2320.1, 2320.2, 2320.3, 2320.4, 2320.5, 2320.6, 2320.7, 2320.8, 2320.9) and a middle layer 2 2330 (represented as 7 nodes 2330.1, 2330.2, 2330.3, 2330.4, 2330.5, 2330.6, 2330.7).

The various input signals are fed into the input layer 2310 on the left. Further hidden layers are used to represent various features of the input as well as non-linear combinations of the inputs. The output layer 2340 combines the signals into a vector representing a position in the 3D space. More (or fewer) middle layers 2320, 2330 may be used, as well as middle layers with a different number of nodes, or a different topology of connections, depending on the nature of the data and the required accuracy of the output.

While this kind of topology may be able to represent any function that maps the inputs to the outputs (Universal Approximation Theorems), in practice some variations of it, or other topologies, may be required, depending on the nature of the data. For example, another NN component may be added, which classifies the inputs into certain classes, and this classification value is fed to the other layers.

As would be understood any number of layers and nodes within the layers may be utilized and the depiction in FIG. 23 is for illustration and understanding only.

In order to provide the input layer 2310 a vector representing a VEC measurement, data from previous patients 2205.1 is used for training the system 2200.1 and training NN 2260.1. For each patient, the data contains measurements consisting of pairs for position of ME (based on EM sensor position) 2220.1 and the VEC for this electrode 2230.1. Additionally, data from previous patients 2205.1 may include Carto 3D model 2210.1 of heart tissue.

This type of data 2205.2 is also required for the online transfer learning stage 2200.2. In order to provide the input layer 2310 a vector representing a VEC measurement, data from the current case 2205.2 is used for fine tuning the system 2200.2 and training NN 2260.2. For each patient, the data contains measurements consisting of pairs for position of ME (based on EM sensor position) 2220.2 and the VEC for this electrode 2230.2. Additionally, data from previous patients 2205.2 may include Carto 3D model 2210.2 of heart tissue.

Because the structure of different hearts vary, and because the location where the patches are placed on the patient also varies, training of the NN 2260 cannot be done on the raw measurements collected from previous patients 2205.1. Registration (alignment) is required, i.e. transforming the raw data into a universal coordinate system (UCS) (2240.1 for previous patients and 2240.2 from the current patient). Given a Carto 3D model 2210.1, 2210.2 of heart tissue, a UCS can be constructed. For example, in each heart chamber, the origin of the UCS may be located exactly at the chamber's center of mass. The x axis may be aligned with a specifically relevant heart structure. The 3D locations in the available data can be shifted, rotated, and stretched, to be transformed to this UCS.

The transformed locations 2240.1, 2240.2 are used with the ME position in UCS 2250.1, 2250.2 as the desired output values of the NN 2260.1, 2260.2. Thus, the raw data 2205.1, 2205.2 is first transformed to the UCS 2240.1, 2240.2 to train 2260.1 the system 2200 and to fine tune 2260.2 the system 2200, and the system 2200 output including the ME position in UCS 2250.3 may be transformed back 2240.3 to the original coordinate system as needed during the inference stage 2200.3 on a new patient.

In the offline stage 2200.1, the NN 2260 is trained 2260.1 on data from previous cases 2205.1. As set forth above, this data may include data consisting of pairs of known 3D position of the Mapping Electrode (after conversion to UCS) 2250.1 and the VEC value 2230.1. The ME position in UCS 2250.1 may be achieved from the Carto 3D Model 2210.1 and the ME position 2220.1 that are transformed to UCS 2240.1. The VEC values 2230.1 serve as input to the NN 2260, and the 3D positions serve as the desired output of the NN 2260.

The dataset of past data 2205.1 may be split into a training set, a validation set, and a test set. The first two sets are to be used during system development, while the test set is used only for evaluating the system's accuracy. Also, cross-validation may be used to improve performance. This incorporates knowledge from past patients 2205.1 into the NN 2260.

After the system 2200 is deployed, additional data may be accumulated and added to the training dataset allowing the system 2200 to re-train and to continually improve its accuracy.

Past data 2205.1 may be insufficient to achieve desired results in training 2260.1 the NN 2260. A standard technique in machine learning is to augment the real data with artificial data produced by a simulation. Systems that are trained on a combination of real data 2205.1 and simulated data may learn better and become more robust than systems that are trained only on real data (provided the simulations are close enough to reality).

There are existing systems that produce high quality simulations of the heart anatomy, including electric currents and how they spread and change as they travel through heart tissue and liquids. These systems can be used to simulate the readings from a catheter as it travels through the heart. The resulting simulated data set can be added to the real data 2205.1.

After training 2260.1 the NN 2260, a trained NN 2270 may be subjected to online fine tuning 2200.2. The trained NN 2270 is fine-tuned 2260.2 using data from the current case 2205.2. As set forth above, this data may include data consisting of pairs of known 3D position of the Mapping Electrode (after conversion to UCS) 2250.2 and the VEC value 2230.2. The ME position in UCS 2250.2 may be achieved from the Carto 3D Model 2210.2 and the ME position 2220.2 that are transformed to UCS 2240.2. The VEC values 2230.2 serve as input to the NN 2260, and the 3D positions serve as the desired output of the NN 2260.

The NN 2270 which is trained on past data 2205.1 may be used "as is" for online inference on a new patient 2205.2. To improve accuracy, fine tuning 2260.2 may be utilized. Fine tuning 2260.2, also known as transfer learning may enable knowledge from previously learned tasks to be reused for the learning of a new task, thus improving accuracy of results. This means that the NN 2260 is continually trained and updated also on data collected from the new patient 2205.2, as it becomes available while the catheter visits new positions of the patient's heart. Due to time constraints, not all the NN's 2260 layers 2320, 2330 are re-trained, but only the last one or two layers. This provides "fine tuning" 2260.2 of the NN 2260 to the particular patient's heart structure and measurements. The fine tuning 2260.2 may be performed after a certain amount of time which is needed for the physician to move the catheter inside the heart to produce at least part of the Carto model 2210.2 of the current patient's heart, as this model is needed for transforming the raw input into the UCS 2240.2. As more measurements are collected for producing the Carto model 2210.2, transformation to the UCS 2240.2 may become more accurate, thus improving the NN's 2260 output.

Once the NN 2260 is fine-tuned 2260.2 on the patient data 2205.2, the inference stage 2200.3 may be entered using thee trained NN 2275. The NN 2260 may be provided the VEC value of an electrode 2230.3, to get the electrode's position in UCS 2250.3. This position then needs to be converted back to the patient's specific coordinate system by transforming from the UCS 2240.3, to get the actual position for the predicted electrode position 2280. In parallel, more data continues to be collected for the current patient 2205.2, and is used to keep fine-tuning 2260.2 the NN 2260.

Since the various chambers in the heart are separate (left/right atria, left/right ventricle, etc.) and have different structures, a separate NN 2260 may be utilized for each such chamber.

Each item in the past dataset 2205.1 contains an indication of which chamber the item was recorded in. Also, during online usage, this indication may come either as a manual indication from the physician, or as automatically based on classification of the catheter's reading using a separate system.

The entire process is done separately on each chamber. However, Transfer Learning 2260.2 may be performed on data across chambers, to improve both accuracy and performance of the NN 2260. The multi-chamber approach may be utilized because during the NN's training 2260.1, 2260.2, lower layers automatically learn to detect basic features, and these are relevant to all chambers.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random-access memory (RAM), a register, cache memory, semiconductor memory devices, magnetic media such as internal hard disks and removable disks, magneto-optical media, and optical media such as CD-ROM disks, and digital versatile disks (DVDs). A processor in association with software may be used to implement a radio frequency transceiver for use in a WTRU, UE, terminal, base station, RNC, or any host computer.

The following non-exhaustive list of embodiments also forms part of the disclosure:

Embodiment 1. A system for automatically generating CPM matrices, comprising:

a plurality of body surface electrodes configured to sense electric signals; and a processor comprising a neural network and configured to:

receive a plurality of historical CPM matrices, patient properties, and corresponding catheter locations;

train a learning system based on the plurality of CPM matrices, patient properties, and corresponding catheter locations;

generate a model based on the learning system;

receive new patient properties at least in part from the plurality of body surface electrodes; and generate new CPM matrices based on new patient properties at least in part from the plurality of body surface electrodes.

Embodiment 2. The system of embodiment 1, wherein the received plurality of historical CPM matrices are based on the known corresponding catheter locations.

Embodiment 3. The system of embodiment 1, wherein the processor is further configured to:

receive a subset of patient properties having known catheter locations; and generate new CPM matrices based also on the subset of patient properties having known catheter locations.

Embodiment 4. The system of embodiment 1, wherein the patient properties are selected from one or more of electrical signals, catheter position, catheter orientation, and heart anatomy.

Embodiment 5. The system of embodiment 4 wherein the patient properties include data from previous patients.

Embodiment 6. The system of embodiment 5 wherein the data from previous patients includes at least one of Carto 3D models, ME position and VEC.

Embodiment 7. The system of embodiment 5 wherein the processor further transforms the Carto 3D models and ME position to UCS.

Embodiment 8. The system of embodiment 1, wherein the learning system is trained using at least one of a classification, regression and a clustering algorithm.

Embodiment 9. The system of embodiment 1 wherein the processor is further configured to transform an ME position in UCS to a predicted electrode position.

Embodiment 10. The system of embodiment 1 wherein the processor is further configured to provide a ME position in UCS based on the training and the VEC for the electrode.

Embodiment 11. A method for generating an arrhythmia prediction model, the method comprising:

receiving a plurality of historical CPM matrices, patient properties, and corresponding catheter locations;

training a learning system based on a first set of historical a plurality of historical CPM matrices, patient properties, and corresponding catheter locations such that combinations of attributes from the historical CPM matrices and patient properties are correlated with a first set of the corresponding catheter locations;

updating the learning system based on a second set of historical a plurality of historical CPM matrices, patient properties, and corresponding catheter locations such that the combinations of attributes from the historical CPM matrices and patient properties are correlated with a second set of corresponding catheter locations; and generating a model based on the first set of the corresponding catheter locations and the second set of corresponding catheter locations.

Embodiment 12. The method of embodiment 11 wherein the second set of corresponding catheter locations are improved based on the first set of corresponding arrhythmia locations.

Embodiment 13. The method of embodiment 11, wherein the received plurality of historical CPM matrices are based on the known corresponding catheter locations.

Embodiment 14. The method of embodiment 11, further comprising: receiving a subset of patient properties having known catheter locations; and generating new CPM matrices based also on the subset of patient properties having known catheter locations.

Embodiment 15. The method of embodiment 11, wherein the patient properties are selected from one or more of electrical signals, catheter position, catheter orientation, and heart anatomy.

Embodiment 16. The method of embodiment 15 wherein the patient properties include data from previous patients.

Embodiment 17. The method of embodiment 16 wherein the data from previous patients includes at least one of Carto 3D models, ME position and VEC.

Embodiment 18. The method of embodiment 17 further comprising transforming the Carto 3D models and ME position to UCS.

Embodiment 19. The method of embodiment 11, wherein the learning system is trained using at least one of a classification, regression and a clustering algorithm.

Embodiment 20. The method of embodiment 11 further comprising:

transforming an ME position in UCS to a predicted electrode position; and providing a ME position in UCS based on the training and the VEC for the electrode.

The following list of aspects also forms part of the disclosure:

Aspect 1. A system for generating improved current-to-position mapping, CPM, matrices, comprising:

a processor configured to:

receive a plurality of historical, sparse CPM matrices and a plurality of historical, supplemented CPM matrices, wherein each sparse CPM matrix is associated with a respective supplemented CPM matrix;

train a learning system based on the plurality of historical, sparse CPM matrices and the plurality of historical, supplemented CPM matrices, wherein the learning system is trained so as to generate a supplemented CPM matrix given a sparse CPM matrix; receive, by the trained learning system, a new, sparse CPM matrix; and generate, with the trained learning system, a new supplemented CPM matrix.

Aspect 2. The system of aspect 1, wherein the processor is further configured to transform an ME position in UCS to a predicted electrode position.

Aspect 3. The system of aspect 1 wherein the processor is further configured to provide a ME position in UCS based on the training and the VEC for the electrode.

Aspect 4. The system of aspect 1, wherein the patient properties are selected from one or more of electrical signals, catheter position, catheter orientation, and heart anatomy Aspect 5. The system of aspect 4 wherein the data from previous patients includes at least one of Carto 3D models, ME position and VEC.

Aspect 6. The system of aspect 5, wherein the processor further transforms the Carto 3D models and ME position to UCS.

What is claimed is:

1. A system for generating improved current-to-position mapping, CPM, matrices, comprising:

a processor configured to:

receive a plurality of historical, sparse CPM matrices and a plurality of historical, supplemented CPM matrices, wherein each historical, sparse CPM matrix is associated with a respective historical, supplemented CPM matrix, each historical, sparse CPM matrix mapping electrical current data to catheter position data at a fewer number of locations than the respective supplemented CPM matrix;

train a learning system based on the plurality of historical, sparse CPM matrices and the plurality of historical, supplemented CPM matrices, wherein the learning system is trained so as to generate a supplemented CPM matrix given a sparse CPM matrix;

receive, by the trained learning system, a new, sparse CPM matrix;

generate, with the trained learning system, a new supplemented CPM matrix based, in part, on the new, sparse CPM matrix; and ablate tissue based, at least in part, on the new supplemented CPM matrix.

2. The system of claim 1, further comprising a plurality of body surface electrodes configured to sense electrical signals.

3. The system of claim 1, wherein receiving the new sparse CPM matrix comprises:

receiving a subset of patient properties having known catheter locations; and generating, from the subset of patient properties and known catheter locations, the new, sparse CPM matrix.

4. The system of claim 1, wherein the processor is configured to:

receive a subset of patient properties without known catheter locations; and determine a catheter location for each of the subset of patient properties without known catheter locations based on said subset of patient properties without known catheter locations and the new, supplemented CPM matrix.

5. The system of claim 3, wherein each catheter location comprises a location of a respective electrode of the catheter.

6. The system of claim 3, wherein the subset of patient properties having known catheter locations and the subset of patient properties without known catheter locations both comprise electrical current signals associated with respective electrodes of the catheter.

7. The system of claim 6, when dependent on claim 2, wherein the electrical current signals associated with respective electrodes of the catheter are sensed by the plurality of body surface electrodes.

8. The system of claim 3 wherein the patient properties of the subset of patient properties having known catheter locations include data from historic procedures.

9. The system of claim 1, wherein the learning system is trained using at least one of a classification, regression and a clustering algorithm.

10. The system of claim 1, wherein the learning system comprises a neural network.

11. A computer-implemented method for generating current-to-position mapping, CPM, matrices, the method comprising:

receiving a plurality of historical, sparse CPM matrices and a plurality of historical, supplemented CPM matrices, wherein each historical, sparse CPM matrix is associated with a respective historical, supplemented CPM matrix, each historical, sparse CPM matrix mapping electrical current data to catheter position data at a fewer number of locations than the respective supplemented CPM matrix;

training a learning system based on a plurality of historical, sparse CPM matrices and the plurality of historical, supplemented CPM matrices, wherein the learning system is trained so as to generate a supplemented CPM matrix given a sparse CPM matrix;

receiving, by the trained learning system, a new, sparse CPM matrix;

generating, with the trained learning system, a new supplemented CPM matrix based, in part, on the new, sparse CPM matrix; and ablating tissue based, at least in part, on the new supplemented CPM matrix.

12. The method of claim 11, wherein receiving a new, spare CPM matrix comprises:

receiving a subset of patient properties having known catheter locations; and generating, from the subset of patient properties and known catheter locations, the new, sparse CPM matrix.

13. The method of claim 11, further comprising:

receiving a subset of patient properties without known catheter locations; and determining a catheter location for each of the subset of patient properties without known catheter locations based on said subset of patient properties without known catheter locations and the new, supplemented CPM matrix.

14. The method of claim 12, wherein each catheter location comprises a location of a respective electrode of the catheter.

15. The method of claim 12, wherein the subset of patient properties having known catheter locations and the subset of patient properties without known catheter locations both comprise electrical current signals recorded at respective electrodes of the catheter.

16. The method of claim 12 wherein the patient properties of the subset of patient properties having known catheter locations include data from historic procedures.

17. The method of claim 11, wherein the learning system is trained using at least one of a classification, regression and a clustering algorithm.

18. The method of claim 14, wherein the learning system comprises a neural network.

\* \* \* \* \*